United States Patent
Inoue

(10) Patent No.: US 10,419,680 B2
(45) Date of Patent: Sep. 17, 2019

(54) ENDOSCOPE SYSTEM AND METHOD OF CONTROLLING ENDOSCOPE SYSTEM

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 228 days.

(21) Appl. No.: 15/239,929

(22) Filed: Aug. 18, 2016

(65) Prior Publication Data

US 2016/0360120 A1    Dec. 8, 2016

Related U.S. Application Data

(63) Continuation of application No. PCT/JP2015/052800, filed on Feb. 2, 2015.

(30) Foreign Application Priority Data

Feb. 21, 2014   (JP) ................... 2014-031246

(51) Int. Cl.
   *A61B 17/00*      (2006.01)
   *A61B 34/20*      (2016.01)
   (Continued)

(52) U.S. Cl.
   CPC ....... *H04N 5/23296* (2013.01); *A61B 1/0005* (2013.01); *A61B 1/00006* (2013.01);
   (Continued)

(58) Field of Classification Search
   CPC .... A61B 5/05; A61B 1/06; A61B 1/09; A61B 1/51; A61B 34/20
   (Continued)

(56) References Cited

U.S. PATENT DOCUMENTS

| | | |
|---|---|---|
| 2007/0265502 A1 | 11/2007 | Minosawa et al. |
| 2008/0086029 A1* | 4/2008 | Uchiyama ............... A61B 1/01 600/114 |

(Continued)

FOREIGN PATENT DOCUMENTS

| | | |
|---|---|---|
| CN | 101416867 A | 4/2009 |
| CN | 102316817 A | 1/2012 |

(Continued)

OTHER PUBLICATIONS

Extended Supplementary European Search Report dated Oct. 5, 2017 received in 15751979.4.

(Continued)

*Primary Examiner* — Patricia I Young
(74) *Attorney, Agent, or Firm* — Scully, Scott, Murphy & Presser, P.C.

(57) ABSTRACT

The endoscope system includes an endoscope including an imaging unit that is capable of taking an image of a subject of interest, a display unit for displaying an image taken by the imaging unit, an endoscopic position sensor for detecting a position of the endoscope in the body cavity, a distance measurement unit for measuring a distance from a distal end of the endoscope to the subject of interest, a position calculation unit for computing the positions of the distal end of the endoscope and the subject of interest on the basis of information from the endoscopic position sensor and the distance measurement unit, a position storage unit for storing a position of the subject of interest computed by the position calculation unit, and a direction indication unit for indicating a direction in which the subject of interest is present on the display unit.

9 Claims, 21 Drawing Sheets

(51) Int. Cl.
*A61B 1/00* (2006.01)
*A61B 90/00* (2016.01)
*H04N 5/232* (2006.01)
*G02B 23/24* (2006.01)
*A61B 5/06* (2006.01)
*H04N 5/225* (2006.01)
*A61B 1/005* (2006.01)
*A61B 1/313* (2006.01)
*A61B 17/34* (2006.01)
*A61B 34/00* (2016.01)

(52) U.S. Cl.
CPC ...... *A61B 1/00009* (2013.01); *A61B 1/00039* (2013.01); *A61B 1/0051* (2013.01); *A61B 1/00071* (2013.01); *A61B 1/00183* (2013.01); *A61B 1/3132* (2013.01); *A61B 5/065* (2013.01); *A61B 90/361* (2016.02); *G02B 23/2476* (2013.01); *G02B 23/2484* (2013.01); *H04N 5/225* (2013.01); *H04N 5/23245* (2013.01); *H04N 5/23293* (2013.01); *A61B 1/00147* (2013.01); *A61B 17/34* (2013.01); *A61B 34/25* (2016.02); *A61B 2034/2046* (2016.02); *A61B 2034/2048* (2016.02); *A61B 2034/2068* (2016.02); *H04N 2005/2255* (2013.01)

(58) Field of Classification Search
USPC .......................................................... 348/65
See application file for complete search history.

(56) References Cited

U.S. PATENT DOCUMENTS

| | | | |
|---|---|---|---|
| 2008/0287783 A1* | 11/2008 | Anderson | A61B 6/12 600/429 |
| 2009/0105726 A1 | 4/2009 | Sugiyama | |
| 2011/0270084 A1 | 11/2011 | Choi et al. | |
| 2014/0323801 A1 | 10/2014 | Konno et al. | |

FOREIGN PATENT DOCUMENTS

| | | | |
|---|---|---|---|
| JP | H10-295639 | A | 11/1998 |
| JP | 2001-204738 | A | 7/2001 |
| JP | 2007-151862 | A | 6/2007 |
| JP | 2007-301378 | A | 11/2007 |
| JP | 2009-100873 | A | 5/2009 |
| JP | 4382894 | B2 | 12/2009 |
| JP | 2011-010841 | A | 1/2011 |
| JP | 2011-234871 | A | 11/2011 |
| JP | 2012-170641 | A | 9/2012 |
| JP | 2013-192773 | A | 9/2013 |
| JP | 5399589 | B2 | 1/2014 |
| WO | WO 20131065473 | A1 | 5/2013 |
| WO | 2013/141404 | A1 | 9/2013 |

OTHER PUBLICATIONS

International Search Report dated Apr. 21, 2015 issued in PCT/JP2015/052800.

* cited by examiner

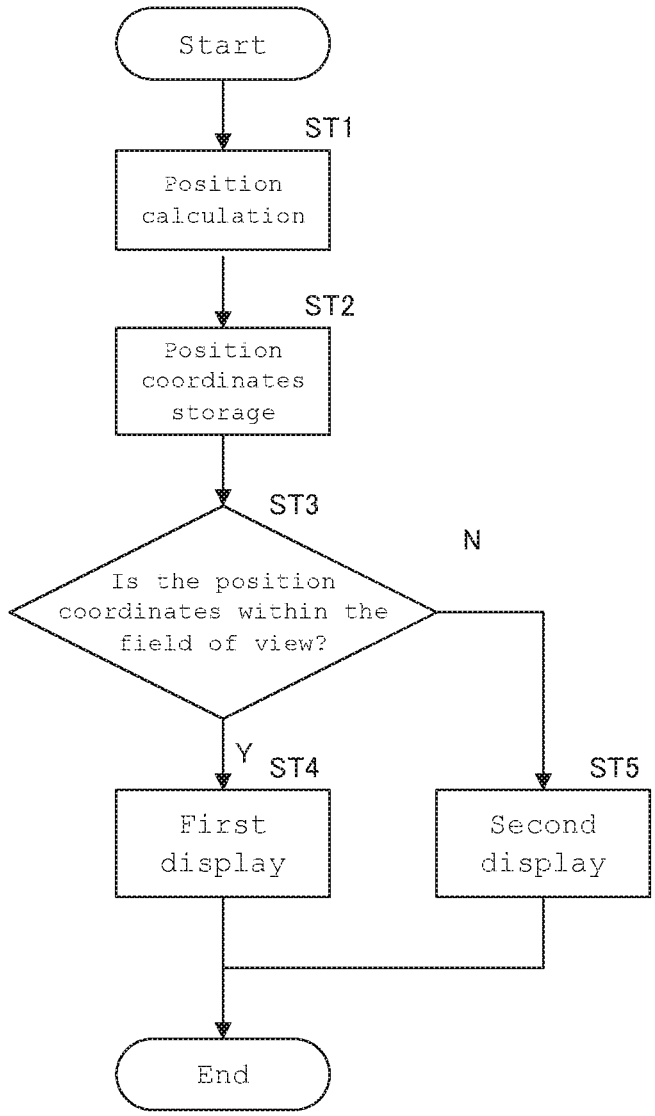

ENDOSCOPE SYSTEM AND METHOD OF CONTROLLING ENDOSCOPE SYSTEM

CROSS-REFERENCE TO RELATED APPLICATIONS

This application is a continuation claiming priority on the basis of Japan Patent Application No. 2014-031246 applied in Japan on Feb. 21, 2014 and based on PCT/JP2015/052800 filed on Feb. 2, 2015. The contents of both the PCT application and the Japan Application are incorporated herein by reference.

BACKGROUND OF THE INVENTION AND RELATED ART STATEMENT

The present invention relates to an endoscope system that is inserted through the body cavity of a patient for surgical operation to view, and apply treatments or the like to, the interior of the patient's body cavity.

In laparoscopic operation, there are multiple incisions cut open in the abdomen or the like of a patient through which various medical instruments such as cameras, forceps and (electric) scalpel are inserted for viewing and treatments of an affected site while checking up with images taken by a camera. This laparoscopic operation is less invasive of the patient because of limited incision area.

In laparoscopic operation, however, some experience and skill is required to keep track of anatomically positional relations between organs in the interior of the body only with recourse to endoscopic images. Especially when there is a wide treatment range, finding a landmark that is an anatomical feature point or reconfirming a bleeding point to which treatment is applied, etc. by operating an endoscope for re-searching purposes becomes a lot of burden to surgeons.

Japanese Patent Publication JP(A) 10-295639 discloses the technology of producing a screen display of the angle of approach on the basis of 3D images taken prior to surgical operation.

Japanese Patent Publication JP(A) 2007-301378 discloses the technology of detecting the tilt angle of a trocar adapted to guide various medical instruments inserted through the abdomen of a patient for the purpose of driving an electrically operated joint in such a way as to allow the area of interest to come in the field of view of an endoscope.

SUMMARY OF INVENTION

According to one embodiment, an endoscope system includes an endoscope including an imaging unit that is capable of taking an image of a subject of interest, a display unit for displaying an image taken by the imaging unit, an endoscopic position sensor for detecting a position of the endoscope in the body cavity, a distance measurement unit for measuring a distance from a distal end of the endoscope to the subject of interest, a position calculation unit for computing positions of the distal end of the endoscope and the subject of interest on the basis of information from the endoscopic position sensor and the distance measurement unit, a position storage unit for storing a position of the subject of interest computed by the position calculation unit, and a direction indication unit for indicating a direction in which the subject of interest is present on the display unit.

According to one embodiment, a method of controlling an endoscope system includes an endoscope having an imaging unit, a display unit for displaying an image from the endoscope, and a trocar for inserting the endoscope into the body cavity, the method includes a position detection step of detecting a position of the endoscope with respect to the trocar, a distance measurement step of measuring a distance from a distal end of the endoscope to a subject of interest, a position calculation step of computing positions of the endoscopic distal end and the subject of interest from the position and the distance, a position storage step of storing the position of the subject of interest, and a direction display step of displaying a direction in which the subject of interest is present on the display unit from the position of the subject of interest.

BRIEF DESCRIPTION OF DRAWINGS

FIG. 5 is illustrative of one example of the control flowchart for the endoscope system according to the first embodiment.

DESCRIPTION OF EMBODIMENTS

Some embodiments will now be explained.

Figure 1:
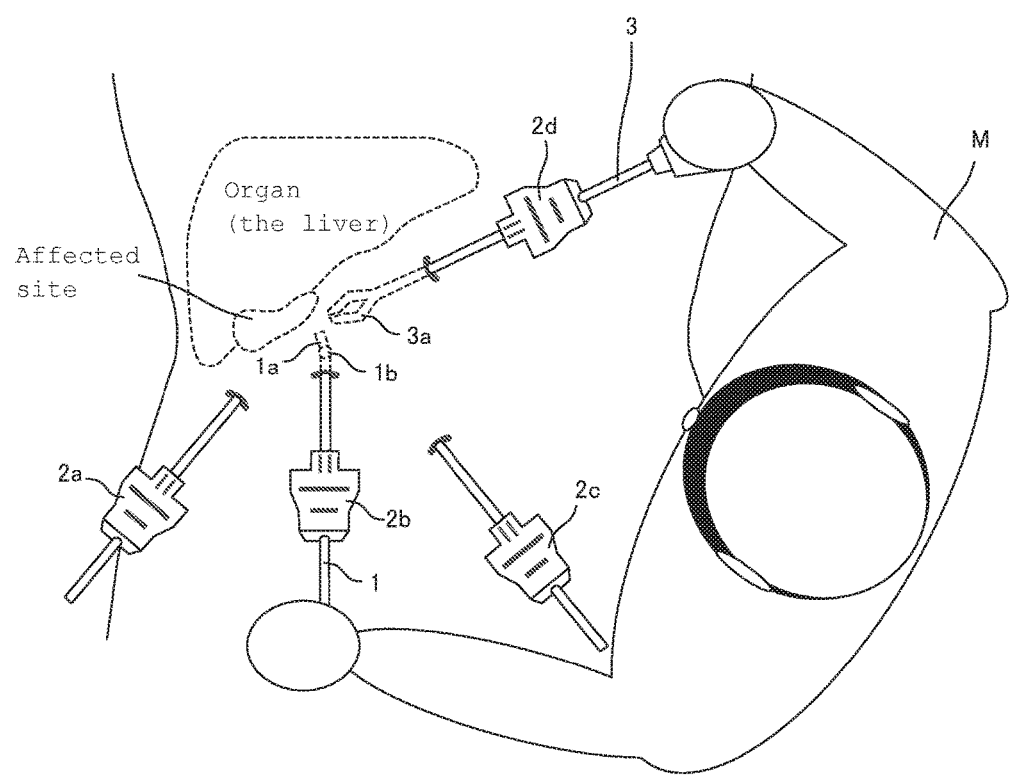
FIG. 1 is a schematic view of one example of the endoscope system according to one embodiment.

FIG. 1 is illustrative in schematic of one example of the endoscope system 10 according to the embodiment described herein.

In laparoscopic surgery, tubes called trocars (channels) 2a to 2d are inserted through incisions cut open in the body wall of a patient, and various medical instruments are inserted into the patient's body cavity by way of such trocars 2a to 2d. FIG. 1 shows that the endoscope 1 is being inserted through the trocar 2b and a treatment tool 3 such as forceps is being inserted through the trocar 2d. The distal end of the endoscope 1 inserted through the patient's body cavity by way of the trocar 2b is provided with an imaging unit 1a and a field of view adjustment mechanism 1b capable of adjusting angles or the like such that an affected site, a treatment tool or the like comes within the field of view. A distal-end portion of the treatment tool 3 inserted into the patient's body cavity by way of the trocar 2d is provided with a distal-end portion 3a such as a grip. A surgeon M adjusts the field adjustment mechanism 1b of the endoscope 1 and operates the treatment tool 3 while viewing images of the affected site taken by the imaging unit 1a, thereby opening or closing the distal-end portion 3a for treatment of the affected site.

Figure 2A:
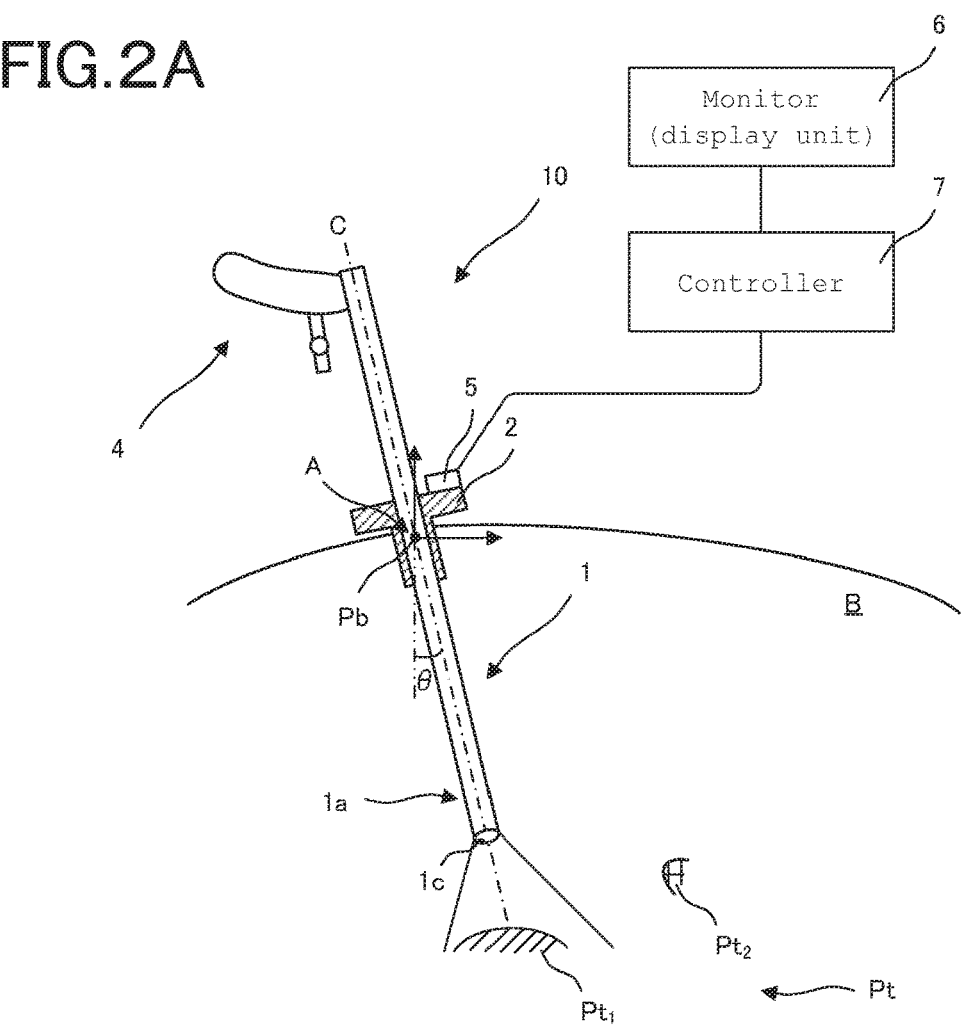
FIGS. 2A and 2B are a schematic view of one example of the endoscope system according to the first embodiment.
Figure 2B:
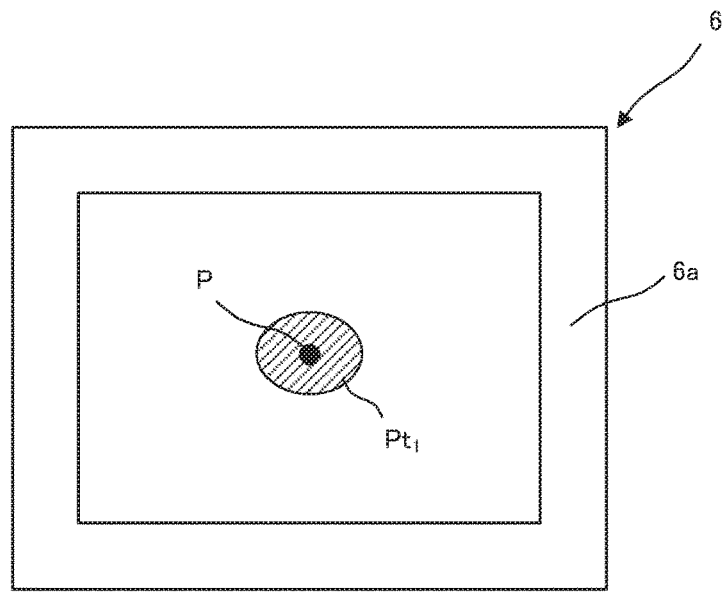
Figure 3:
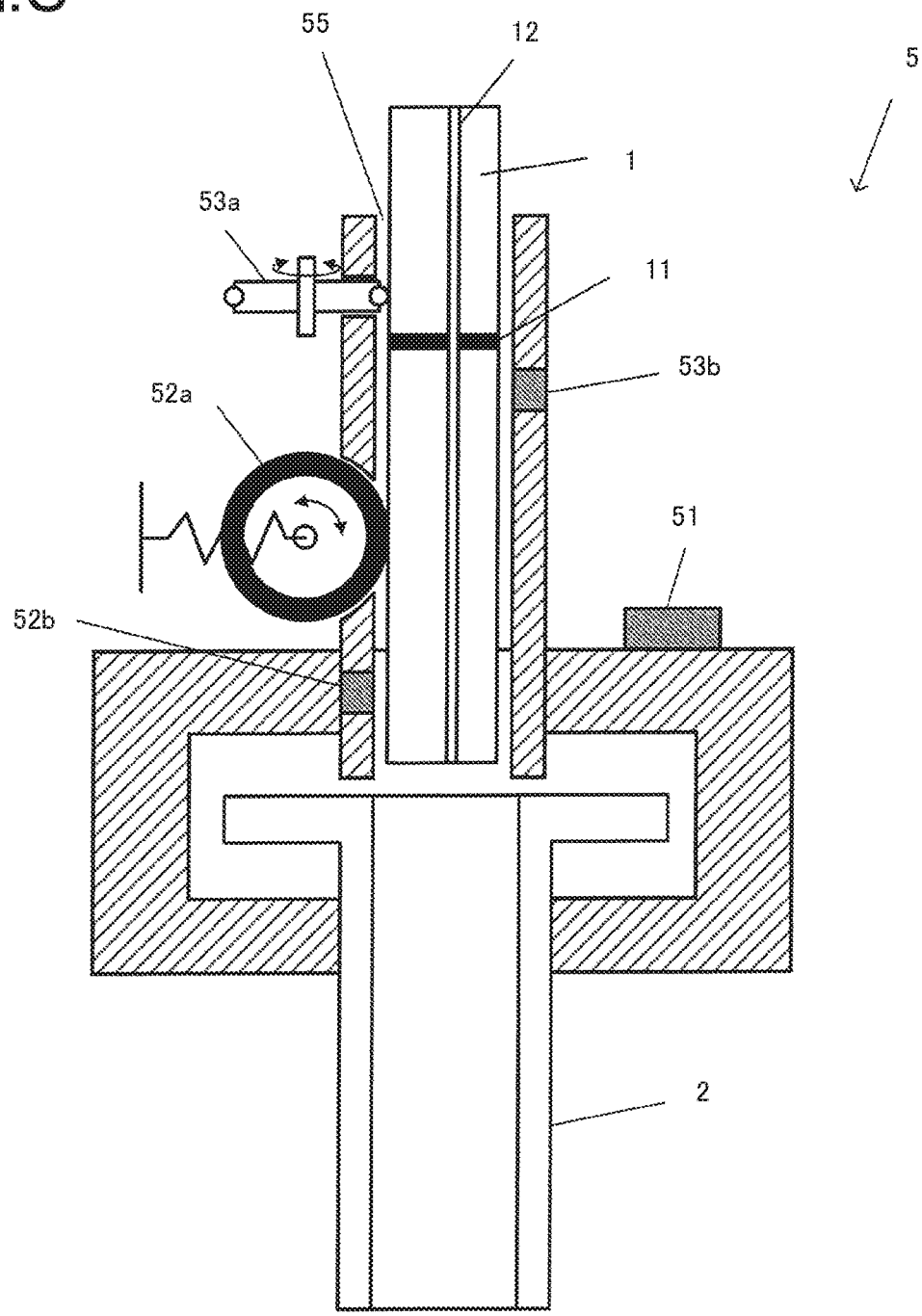
FIG. 3 is a schematic view of the trocar sensor in the endoscope system according to the first embodiment.

FIGS. 2A and 2B are illustrative in schematic of one example of the endoscope system 10 according to the first embodiment: FIG. 2A shows that the endoscope 1 of the endoscope system 10 according to the first embodiment is being inserted through the body cavity B way of the trocar 2, and FIG. 2B shows images appearing on the display unit in the state of FIG. 2A. FIG. 3 is illustrative in schematic of the trocar sensor 5 in the endoscope system 10 according to the first embodiment.

The endoscope 1 is inserted into the body cavity B through the trocar 2. In the endoscope 1, the imaging unit 1a of the endoscope 1 is directed to the first subject of interest $Pt_1$ or the second subject of interest $Pt_2$ by operation of the operation input unit 4. The imaging unit 1a is provided with a distance sensor 1c that works as a position sensor adapted to measure a distance to the subject of interest Pt.

The trocar 2 according to the embodiment described herein includes a trocar sensor 5, as depicted in FIG. 3. The trocar sensor 5 includes, and is constructed of, a tilt angle detection sensor 51, an amount-of-advanceable/retractable-movement detection sensor 52 and an amount-of-rotation detection sensor 53.

The tilt angle detection sensor 51 is provided to detect in which direction the trocar 2 turns with respect to a reference coordinate system. The reference coordinate system here is the one that is defined relative to a fixed object such as a patient or the ground; for instance, there is the mention of a coordinate system A with the fulcrum Pb of FIG. 2A as center. A variety of sensors such as an acceleration sensor may be used as the tilt angle detection sensor 51. The acceleration sensor may detect an acceleration applied thereon to detect in which direction the trocar 2 turns, that is, the tilt angle θ of the trocar 2 with respect to such a coordinate system as shown in FIG. 2A.

The amount-of-advanceable/retractable-movement detection sensor 52 is provided for detection of the amount of advanceable/retractable movement of a medical instrument such as the endoscope 1 inserted through the trocar 2 in its insertion direction. A surgeon such as a physician inserts or deinserts a medical instrument through the trocar 2 to operate and move the medical instrument within the patient's body to an unerring position. With the amount-of-advanceable/retractable-movement detection sensor 52, it is possible to detect the insertion position of the medical instrument relative to the trocar 2 in the form of the amount of advanceable/retractable-movement. FIG. 2A shows the center axis C of the trocar 2 in the insertion direction by a dashed line. The amount-of-advanceable/retractable-movement detection sensor 52 detects the amount of movement parallel with that center axis C in the form of the amount of advanceable/retractable movement. In the embodiment described herein, the amount-of-advanceable/retractable-movement detection sensor 52 is made up of a combined amount-of-advanceable/retractable-movement detection roller 52a and photosensor 52b. Preferably in this case, the medical instrument such as the endoscope 1 is provided with an advanceable/retractable position detection mark 11 that is capable of being detected by the photosensor 52b.

The amount-of-rotation detection sensor 53 is provided for detection of the amount of rotation of a medical instrument that rotates in association with operation as by a surgeon. By rotational operation about the center axis C of a medical instrument inserted through the insertion hole 55, it is possible to change the orientation of an end effector mounted at the distal end of the medical instrument within the patient's body. The amount-of-rotation detection sensor 53 detects this amount of rotation so that in which direction the end effector of the medical instrument turns can be detected. The amount-of-rotation detection sensor 53 here is made up of a combined amount-of-rotation detection roller 53a and photosensor 53b. Preferably in this case, the medical instrument such as the endoscope 1 is provided with an advanceable/retractable position detection mark 12 that is capable of being detected by the photosensor 53b.

While the trocar sensor 5 located in the trocar 2 has been explained, it is to be understood that sensors having various forms may be used instead. For instance, a mechanical sensor using a roller is here used for the purpose of detecting the amount of advanceable/retractable movement and rotation, but the amount of advanceable/retractable movement and rotation may also be detected by means of an optical sensor capable of detecting the amount and direction of movement of a surface used for a laser mouse. In that case, a single optical sensor may be used for the detection of the amounts of movement and rotation. For the medical system according to the embodiment described herein, it is required to know the direction or the direction and position of a medical instrument inserted through the body of a patient. In the embodiment described herein, these are easy to detect because various sensors are located within the trocar 2; however, an external sensor located outside the trocar 2 may be used to detect the direction or the direction and position of the medical instrument. For instance, the tilt angle detection sensor 51 located in the trocar 2 may be provided directly on the medical instrument side.

When the endoscope 1 is placed as shown in FIG. 2A, there is such an image of the first subject of interest $Pt_1$ as shown in FIG. 2B appearing on the display unit 6 such as a monitor.

Figure 4:
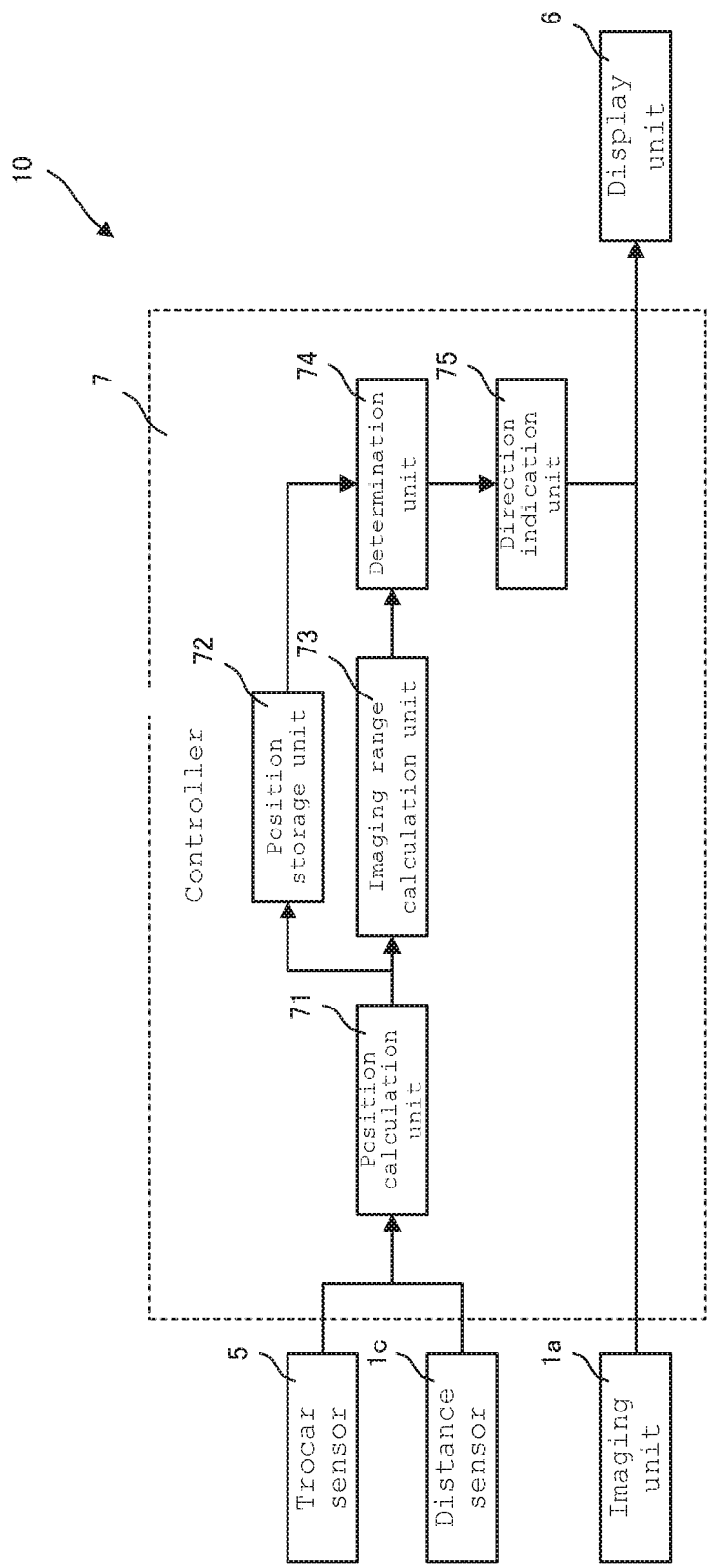
FIG. 4 is illustrative of one example of the control system for the endoscope system according to the first embodiment.

FIG. 4 is illustrative of one example of the control system for the endoscope system 10 according to the first embodiment.

The endoscope system 10 is controlled by a controller 7. A position calculation unit 71 is adapted to compute the position of the subject of interest Pt shown in FIG. 2A on the basis of information entered from the trocar sensor 5 and distance sensor 1c. A position storage unit 72 is adapted to store the position of the subject of interest Pt computed by the position calculation unit 71. An imaging range calculation unit 73 is adapted to compute the imaging range of the endoscope 1, and a determination unit 74 is provided to determine whether or not the position of the subject of interest Pt stored in the position storage unit 72 is included within the imaging range of the endoscope 1 found by the imaging range calculation unit 73. A direction indication unit 75 is designed such that when the position of the subject of interest Pt stored in the position storage unit 72 is not included in the field of view of the endoscope, there is the direction of the position of the subject of interest Pt indicated.

Figure 6A:
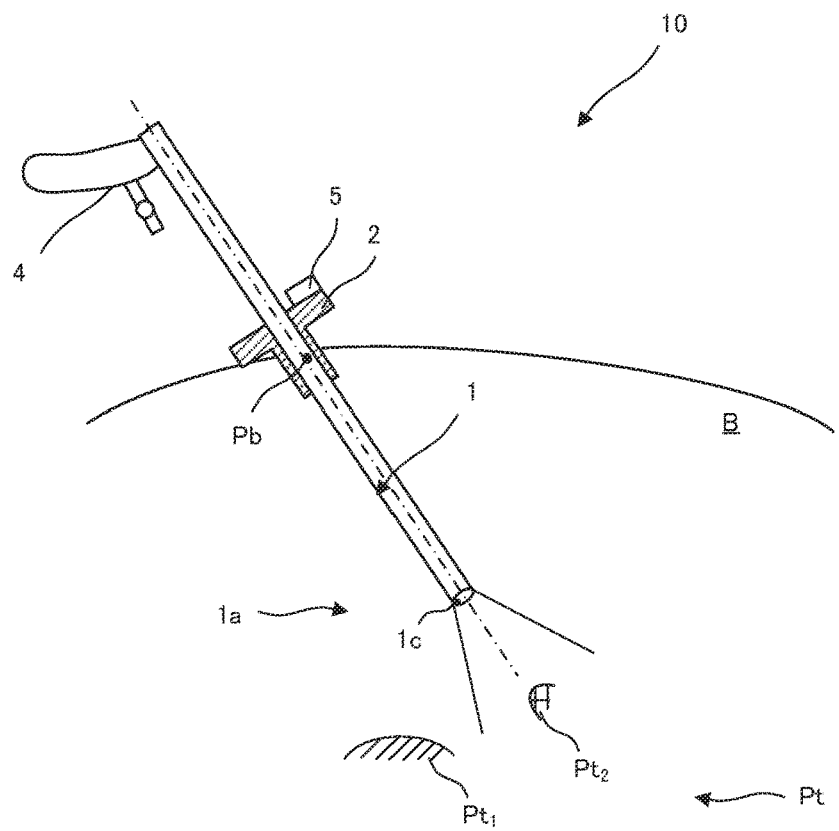
FIGS. 6A and 6B are illustrative of the endoscope according to the first embodiment directed to the second subject of interest and the then display unit.
Figure 6B:
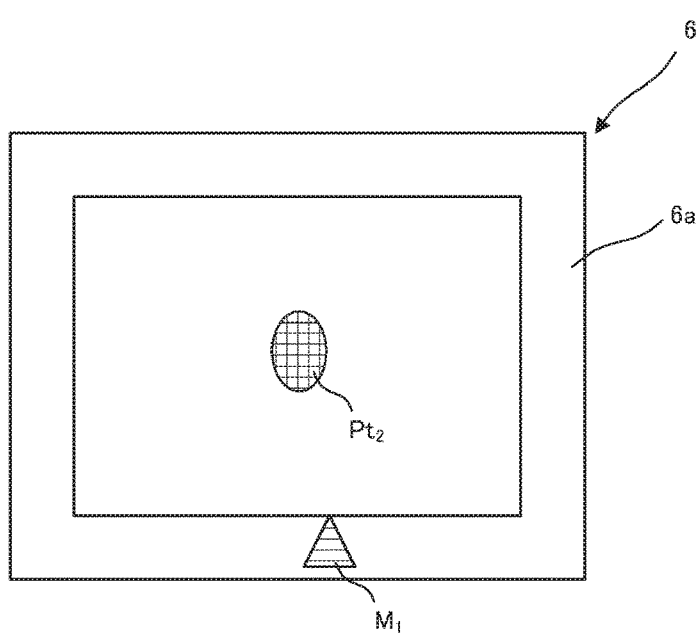

FIG. 5 is illustrative of one example of the control flowchart for the endoscope system 10 according to the first embodiment. FIGS. 6A and 6B are illustrative of the endoscope 1 according to the first embodiment directed to the second subject of interest $Pt_2$ and the then display unit: FIG. 6A is illustrative of the endoscope 1 according to the first embodiment directed to the second subject of interest $Pt_2$ and FIG. 6B is illustrative of the then display unit 6.

Referring to the endoscope system 10 according to the first embodiment, the position of the first subject of interest $Pt_1$ shown in FIGS. 2A and 2B is first computed by the position calculation unit 71 in Step 1 on the basis of information entered from the trocar sensor 5 and distance sensor 1c (ST1).

Then, the processing goes to Step 2 in which the position of the first subject of interest $Pt_1$ computed by the position calculation unit 71 is stored in the position storage unit 72 (ST2).

Suppose here that the endoscope 1 is directed by the surgeon to the second subject of interest $Pt_2$ for viewing, as shown in FIG. 6A.

In the state shown in FIG. 6A, the processing goes to Step 3 in which it is determined whether or not the position of the first subject of interest $Pt_1$ stored in the position storage unit 72 is within the imaging range (ST3).

In Step 3, when the position of the first subject of interest $Pt_1$ is within the imaging range, the processing goes to Step 4 in which a first display pattern is displayed on the display unit 6, defining a point mark P indicative of the first subject of interest $Pt_1$ (ST4) as shown in FIGS. 2A and 2B: the control gets done.

In Step 3, when the position of the first subject of interest $Pt_1$ is not in the imaging range, the processing goes to Step 5 in which a second display pattern is displayed on the edge 6a of the display unit 6, defining a first direction indication mark $M_1$ (ST5), as shown in FIG. 6B: the control gets done.

The first direction indication mark $M_1$ is displayed in a direction in which the first subject of interest $Pt_1$ is present on the edge 6a of the display unit 6. The surgeon can take a look at the first direction indication mark $M_1$ to keep track of the direction in which the first subject of interest $Pt_1$ is present.

Figure 7:
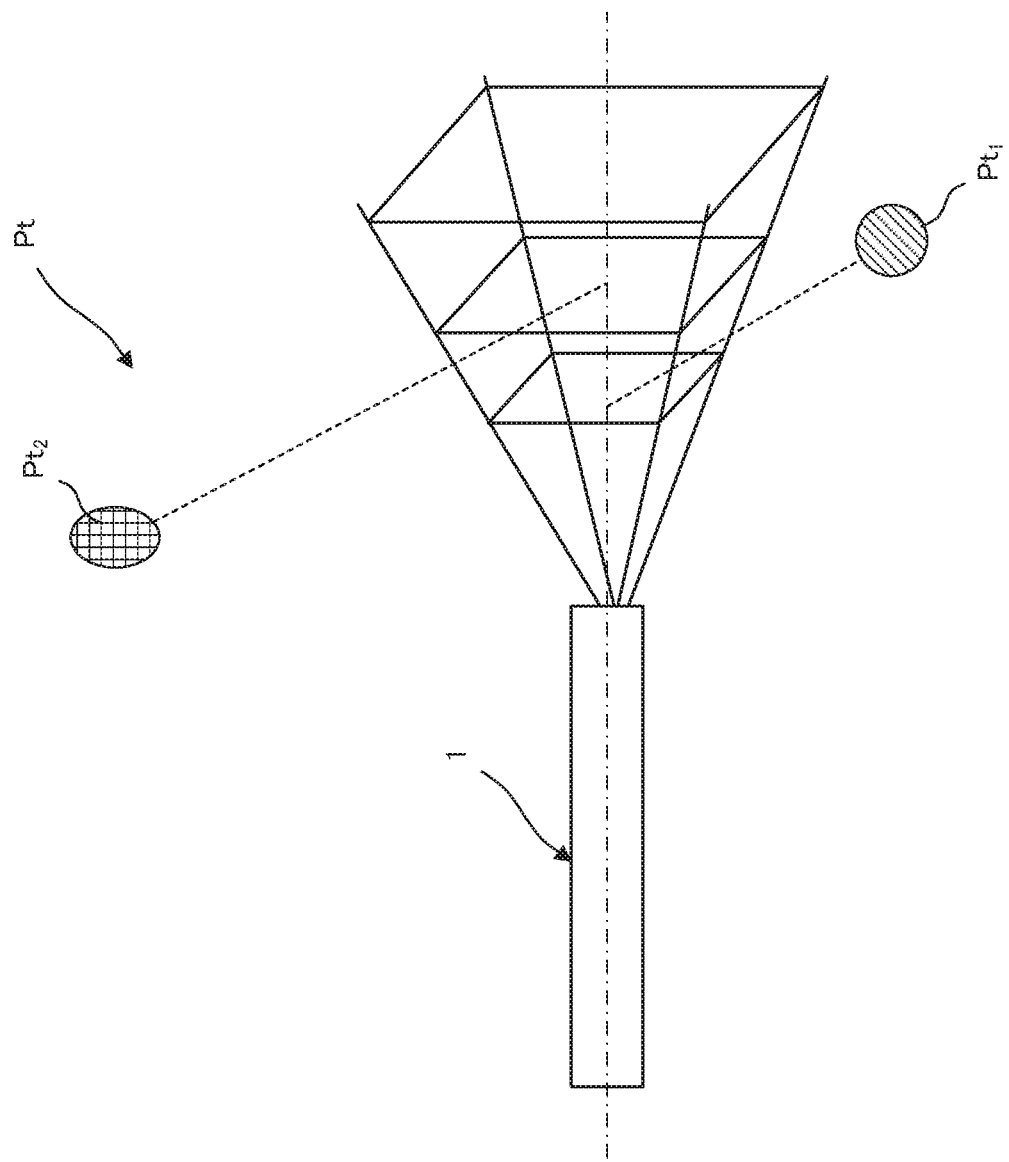
FIG. 7 is illustrative of one exemplary positional relation between the endoscope and the subject of interest in the first embodiment.
Figure 8:
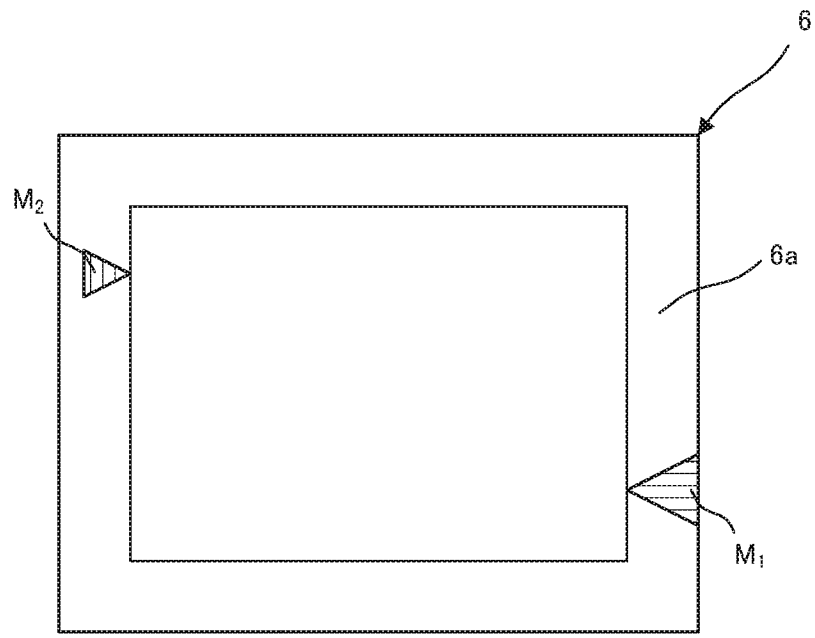
FIG. 8 is illustrative of one example of how to produce a display by the display unit according to the first embodiment.

FIG. 7 is illustrative of one exemplary positional relation of the endoscope 1 to the subject of interest Pt in the first embodiment, and FIG. 8 is illustrative of one example of how to produce a screen display on the display unit 6 according to the first embodiment.

When there is the field of view of the endoscope 1 present between the first $Pt_1$ and the second subject of interest $Pt_2$ as shown in FIG. 7, the first direction indication mark $M_1$ is displayed in the direction in which there is the first subject of interest $Pt_1$ present, and the second direction indication mark $M_2$ is displayed in the direction in which there is the second subject of interest $Pt_2$ present, as shown in FIG. 8. In the example shown in FIG. 7, there is the first subject of interest $Pt_1$ relatively near to the field of view, and there is the second subject of interest $Pt_2$ away from the field of view. In this case, as the first direction indication mark $M_1$ displayed is larger than the second direction indication mark $M_2$ as shown in FIG. 8, it is possible for the surgeon to keep track of distance information in addition to direction information and, hence, take an unerring track of the positions of the first $Pt_1$ and the second subject of interest $Pt_2$. Note here that the distance information may be displayed not only in varying size but also in varying color and shape together with characters, numerals or the like nearby.

Figure 9:
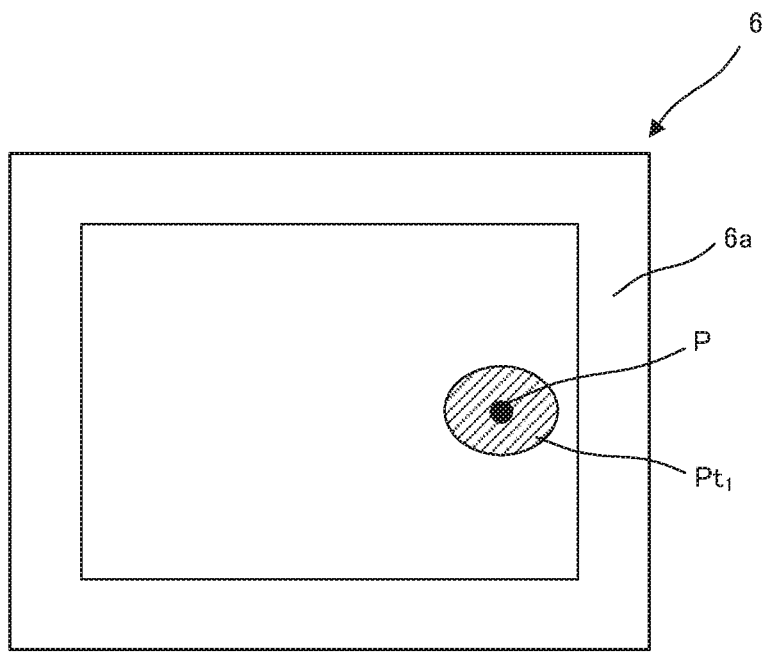
FIG. 9 is illustrative of one example of how to produce a display by the display unit according to the first embodiment when there is the first subject of interest present within the field of view of the endoscope according to the first embodiment.

FIG. 9 is illustrative of one example of how to produce a screen display on the display unit 6 in a state where there is the first subject of interest $Pt_1$ within the field of view of the endoscope 1 according to the first embodiment.

When there is the first subject of interest $Pt_1$ in the field of view of the endoscope 1, the point mark P may be displayed while superimposed on the image of the first subject of interest $Pt_1$ in the display unit 6. It is thus possible to keep immediate track of the presence of the first subject of interest $Pt_1$ because the point mark P is displayed while superimposed on the image of the first subject of interest $Pt_1$ in the display unit 6.

As described above, the endoscope system 10 according to the first embodiment includes an endoscope 1 including an imaging unit 1a that is capable of taking an image of a first subject of interest $Pt_1$, a display unit 6 for displaying an image taken by the imaging unit 1a, an endoscopic position sensor 5 for detecting a position of the endoscope 1 in the body cavity, a distance measurement unit 1c for measuring a distance from a distal end of the endoscope 1 to the subject of interest Pt, a position calculation unit 71 for computing the positions of the distal end of the endoscope and the subject of interest Pt on the basis of information from the endoscopic position sensor 5 and the distance measurement unit 1c, a position storage unit 72 for storing a position of the subject of interest Pt computed by the position calculation unit 71, and a direction indication unit 75 for indicating a direction in which the subject of interest Pt is present on the display unit 6. It is thus possible to indicate the direction of the subject of interest Pt thereby easily keeping track of the position of the subject of interest Pt.

The endoscope system 10 further includes an imaging range calculation unit 73 for computing an imaging range of the imaging unit 1a, and a determination unit 74 for determining whether or not the position of the first subject of interest $Pt_1$ is within the imaging range, wherein when the position of the subject of interest Pt is determined by the determination unit 74 as being outside the imaging range, the direction indication unit 75 displays a direction indication mark indicative of a direction in which the subject of interest Pt is present on the display unit 6. It is thus possible to indicate the direction of the subject of interest Pt thereby keeping unerring track of the position of the subject of interest Pt, even when the subject of interest Pt is not displayed.

Further, the process of controlling an endoscope system including an endoscope 1 having an imaging unit 1a, a display unit 6 for displaying an image from the endoscope 1, and a trocar 2 for inserting the endoscope 1 into the body cavity includes a position detection step of detecting a position of the endoscope 1 with respect to the trocar 2, a distance measurement step of measuring a distance from a distal end of the endoscope 1 to a subject of interest, a position calculation step of computing the positions of the distal end of the endoscope 1 and the subject of interest from that position and that distance, a position storage step of storing the position of the subject of interest, and a direction display step of displaying a direction in which the subject of interest is present on the display unit 6 from the position of the subject of interest. It is thus possible to indicate the direction of the subject of interest Pt thereby easily keeping track of the position of the subject of interest Pt.

Figure 10A:
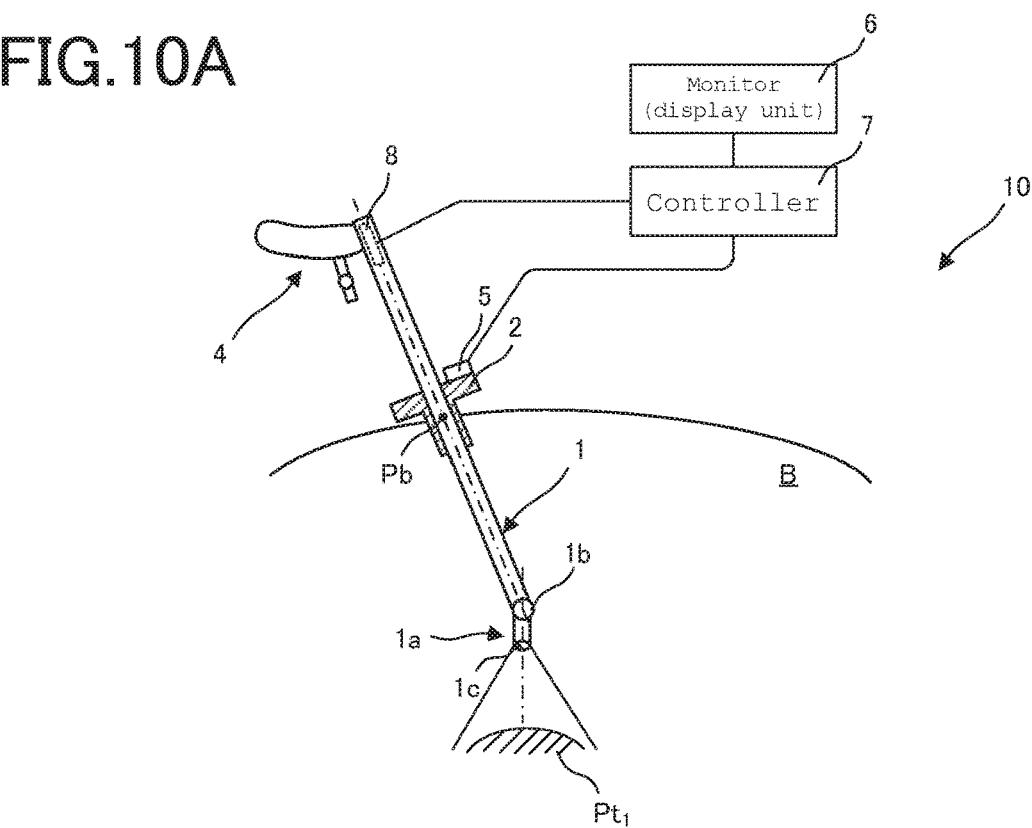
FIGS. 10A and 10B are a schematic view of one example of the endoscope system 10 and display unit according to the second embodiment.
Figure 10B:
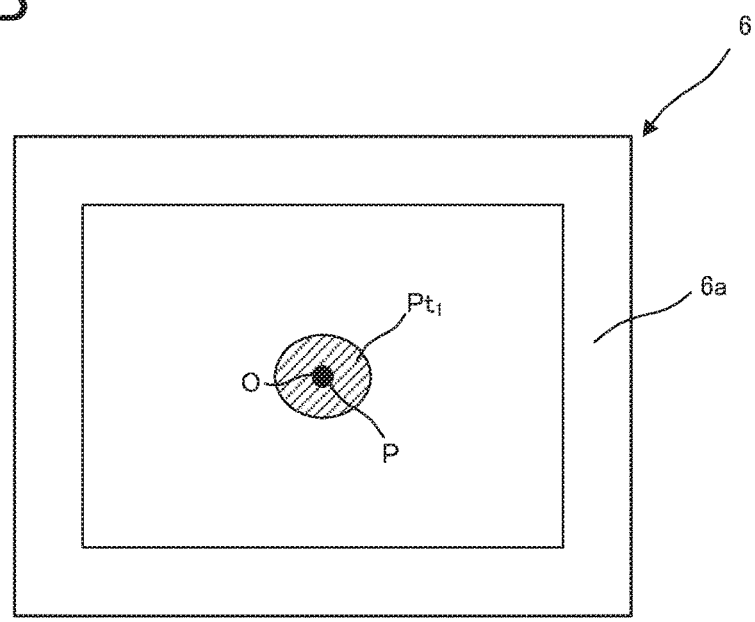

FIGS. 10A and 10B are illustrative in schematic of one example of the endoscope system 10 and display unit according to the second embodiment: FIG. 10A is a schematic view of one example of the endoscope system 10 according to the second embodiment and FIG. 10B is a schematic view of one example of the display unit in the endoscope system 10 according to the second embodiment.

The endoscope 1 is inserted into the body cavity B through the trocar 2. Referring to the endoscope 1, the field adjustment mechanism 1b is adjusted by operation of the operation input unit 4 to direct the imaging unit 1a to the first subject of interest $Pt_1$. The imaging unit 1a is provided with a distance sensor 1c working as a position sensor for measuring a distance to the first subject of interest $Pt_1$.

The trocar 2 is rotatable about a fulcrum Pb, and the trocar sensor 5 working as a position sensor is capable of detecting at least the tilt angle of the trocar 2, the amount of insertion of the endoscope 1 into the trocar 2, and the angle of rotation of the endoscope 1 with respect to a center axis.

In the second embodiment, while the distance sensor 1c and trocar sensor 5 are used as the position sensor, it is to be understood that other sensors may be used with the proviso that they are capable of detecting the position of the endoscope 1 in the body cavity B. The field adjustment mechanism 1b preferably includes at least one rotatable electrically operated joint. The electrically operated joint more preferably includes a succession of multiple joints, because of making improvements in the directionality of the imaging unit 1a. The field adjustment mechanism 1b may be located outside the body cavity.

Figure 11:
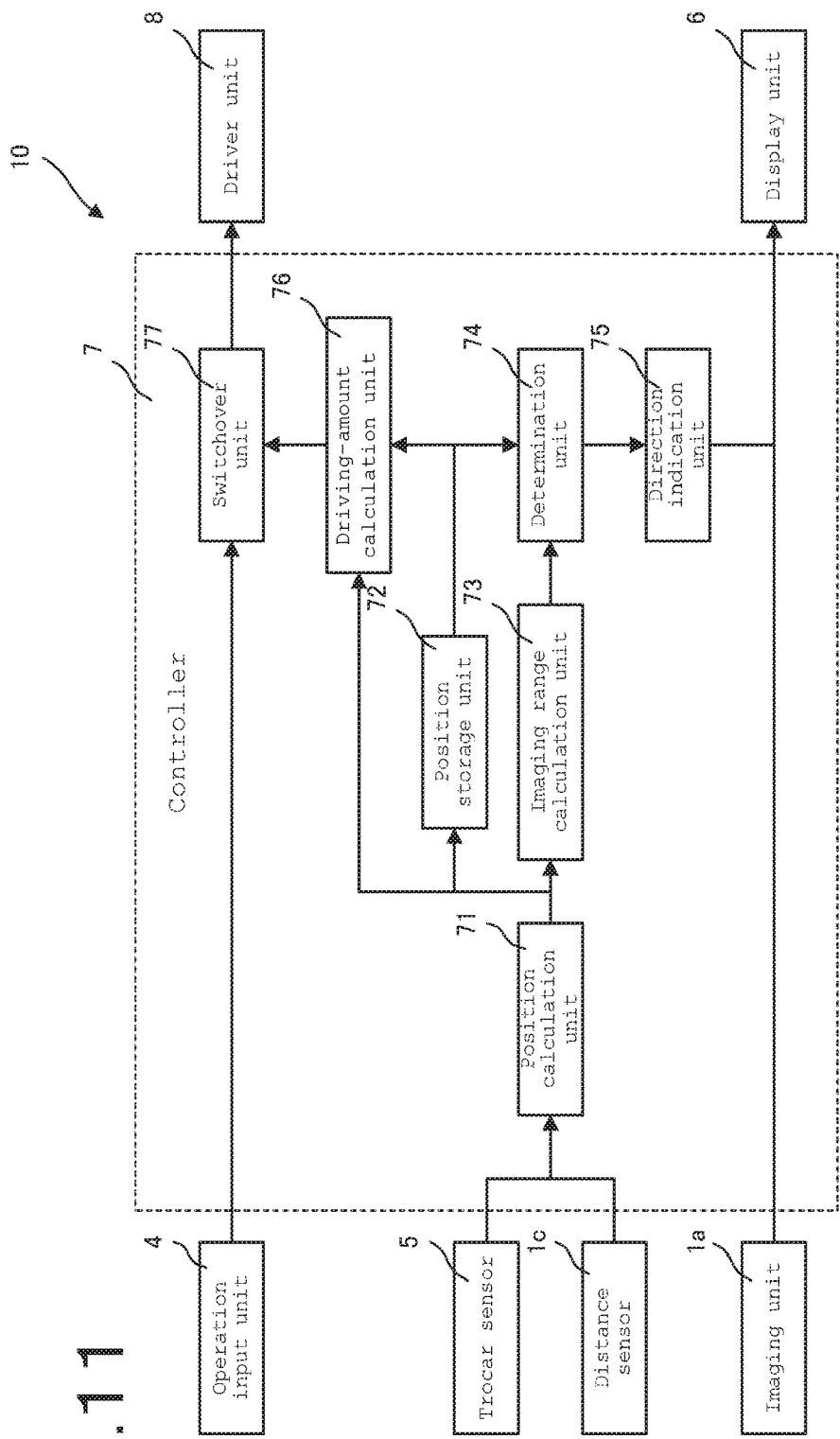
FIG. 11 is illustrative of one example of the control system for the endoscope system 10 according to the second embodiment.

FIG. 11 is illustrative of one example of the control system for the endoscope system 10 according to the second embodiment.

Referring here to the endoscope system 10 according to the second embodiment, the position calculation unit 71, position storage unit 72, imaging range calculation unit 73, determination unit 74 and direction indication unit 75 will not be explained anymore because of being similar to those in the first embodiment.

The driving amount for the driver unit 8 that drives the field adjustment mechanism 1b of FIGS. 10A and 10B are computed by the driving-amount calculation unit 76 such that at least a part of the position of the first subject of interest $Pt_1$ includes the center of the field of view. The driver unit 8 may be directly rotated as by an electric motor that rotates the joint of the field adjustment mechanism 1b or indirectly done by way of a wire or the like.

The switchover unit 77 is adapted to switch between a normal mode and a tracking mode in response to an input signal from the operation input unit 4. In the normal mode, the field of view moves together with the imaging unit 1a, and in the tracking mode, the first subject of interest $Pt_1$ remains fixed within the field of view even when the imaging unit 1a is on the move.

Figure 12:
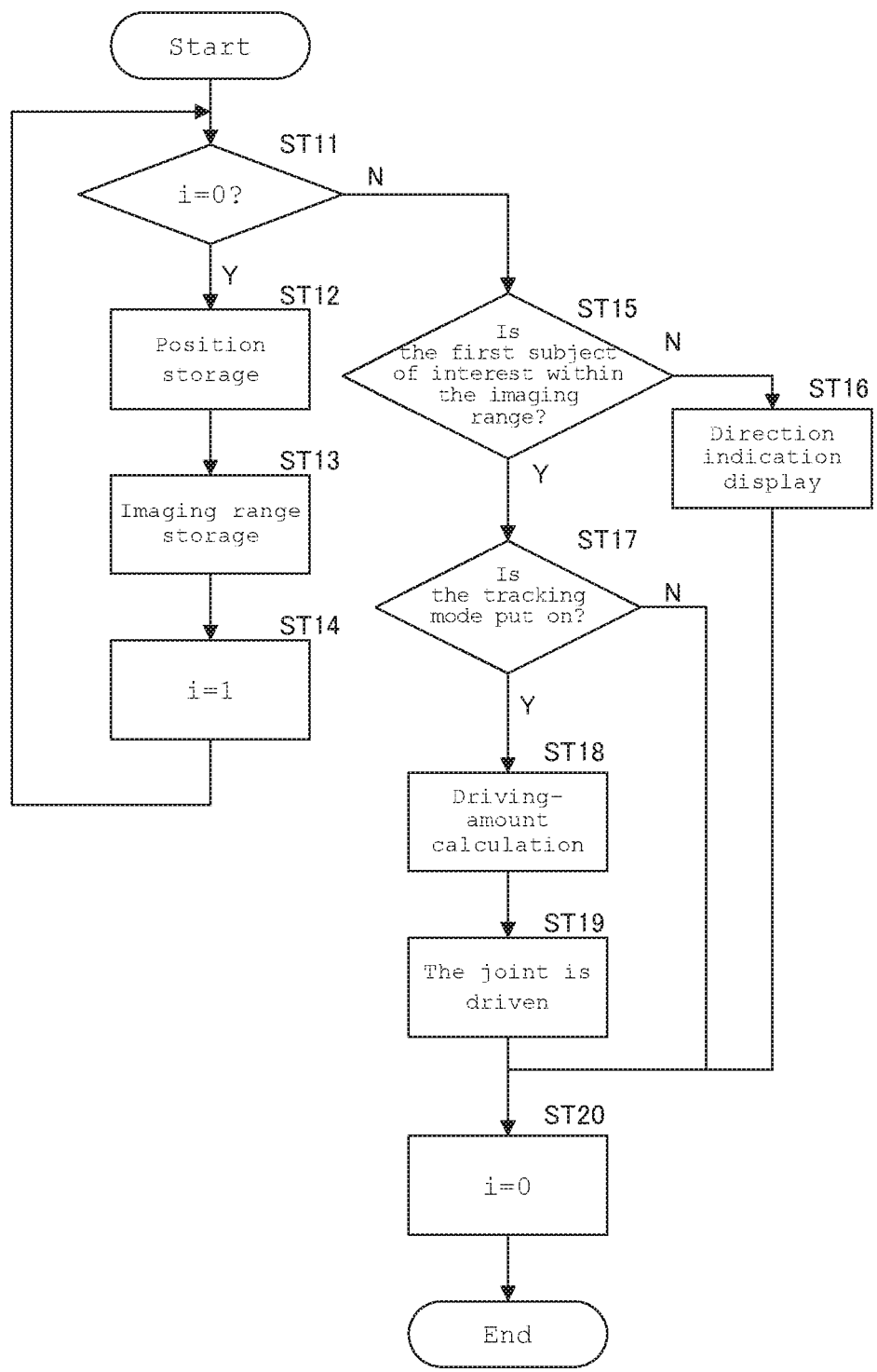
FIG. 12 is illustrative of one example of the control flowchart for the endoscope system according to the second embodiment.

FIG. 12 is illustrative of one example of the control flowchart for the endoscope system 10 according to the second embodiment.

Referring to the endoscope system 10 according to the second embodiment, it is first determined in Step 11 whether or not the counter is i=0 (ST11).

In Step 11, when the counter is i=0, the processing goes to Step 12 in which there is such a state as shown in FIGS. 10A and 10B appearing: the positions of the distal end of the endoscope and the first subject of interest $Pt_1$ are computed by the position calculation unit 71 on the basis of information entered from the trocar sensor 5 and distance sensor 1c and then stored in the position storage unit 72 (ST12).

Then, the processing goes to Step 13 in which the imaging range is computed by the imaging range calculation unit 73 (ST13).

Then, the processing goes to Step 14 in which the counter is set to i=1 (ST14), and goes back to Step 11.

In Step 11, when the counter is not i=0, the processing goes to Step 15 in which it is determined whether or not the first subject of interest $Pt_1$ lies within the imaging range computed by the imaging range calculation unit 73 (ST15).

In Step 15, when the first subject of interest $Pt_1$ is not within the imaging range, the processing goes to Step 16 in which the direction indication mark $M_1$ is displayed (ST16), and then goes to Step 20.

In Step 15, when there is the first subject of interest Pt1 in the imaging range, the processing goes to Step 17 in which it is determined whether or not the tracking mode is held on by the switchover unit 77 (ST17).

In Step 17, when the tracking mode is held off by the switchover unit M the processing goes to Step 20.

In Step 17, when the tracking mode is held on by the switchover unit 77, the processing goes to Step 18 in which the driving amount computed by the driving-amount calculation unit 76 is computed (ST18), and then goes to Step 19 in which the field adjustment mechanism 1b is driven according to the computed driving amount (ST19).

Figure 13A:
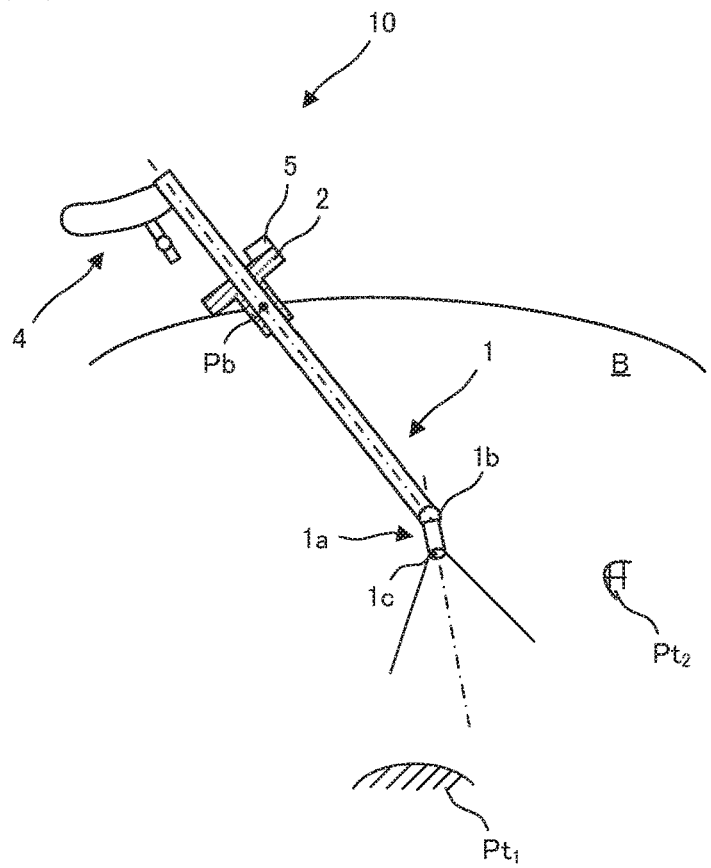
FIGS. 13A and 13B are illustrative of the endoscope in a state where there is the first subject of interest present in the imaging range after movement of the endoscope system according to the second embodiment.
Figure 13B:
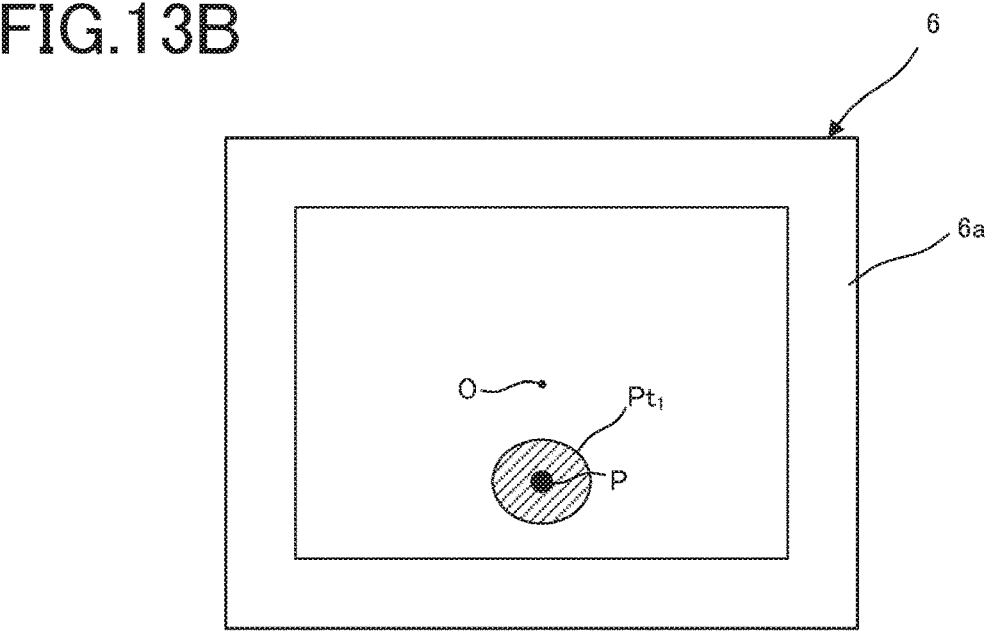

FIGS. 13A and 13B are illustrative of the endoscope 1 in the case where the first subject of interest $Pt_1$ is within the imaging range after movement of the endoscope system 10 according to the second embodiment and the then display unit: FIG. 13A is illustrative of the endoscope system 10 and FIG. 13B is illustrative of the display unit 6.

Figure 14A:
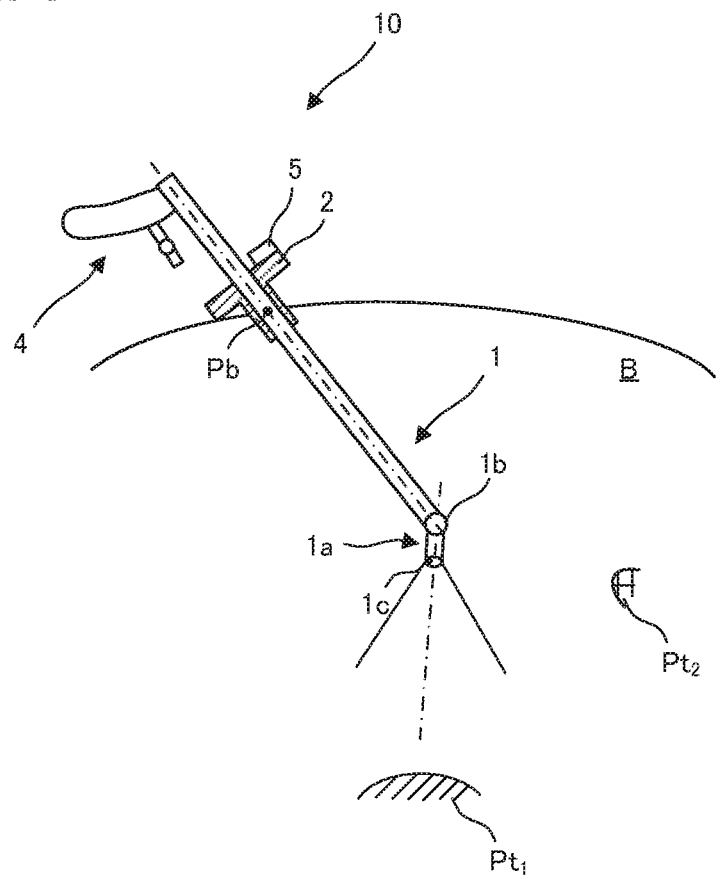
FIGS. 14A and 14B are illustrative of the endoscope in a state after movement of the endoscope system according to the second embodiment and after the field adjustment mechanism is driven.
Figure 14B:
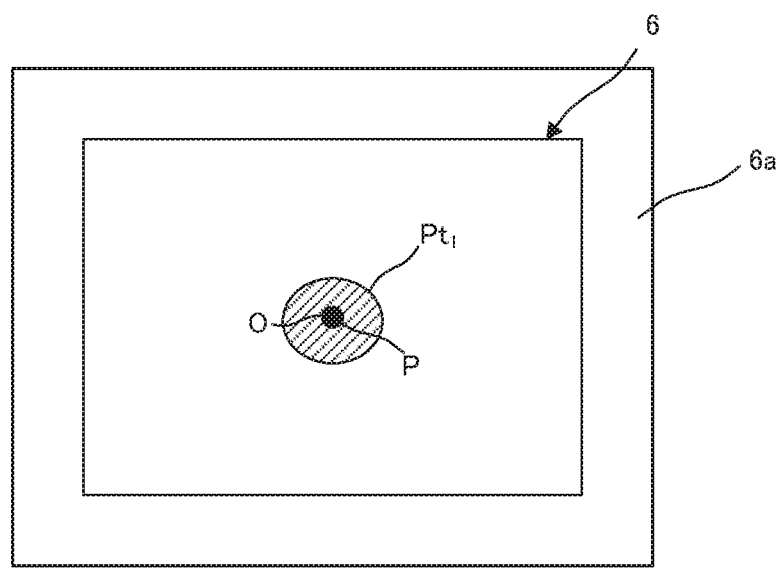

FIGS. 14A and 14B are illustrative of the endoscope 1 after movement of the endoscope system 10 according to the second embodiment and the field adjustment mechanism 1b is driven and the then display unit 6: FIG. 14A is illustrative of the endoscope system 10 and FIG. 14B is illustrative of the display unit 6.

As the endoscope 1 is moved by the surgeon from the storage position of FIG. 10A to a position within the imaging range shown in FIG. 13A, an image of the first subject of interest $Pt_1$ looks like as shown in FIG. 13B.

Here the direction and amount of moving the current first subject of interest $Pt_1$ in such a way as to include at least the center O of the screen, just like the first subject of interest $Pt_1$ of FIG. 14B, are computed by the driving-amount calculation unit 76. That is, the driving amount for driving the field adjustment mechanism 1b is computed by the driving-amount calculation unit 76.

After that, the field adjustment mechanism 1b is driven, as shown in FIG. 14A, to vary the orientation of the imaging unit 1a so that the current first subject of interest $Pt_1$ is nearly centered in such as a way as to include at least the center O of the screen, as shown in FIG. 14B.

Figure 15A:
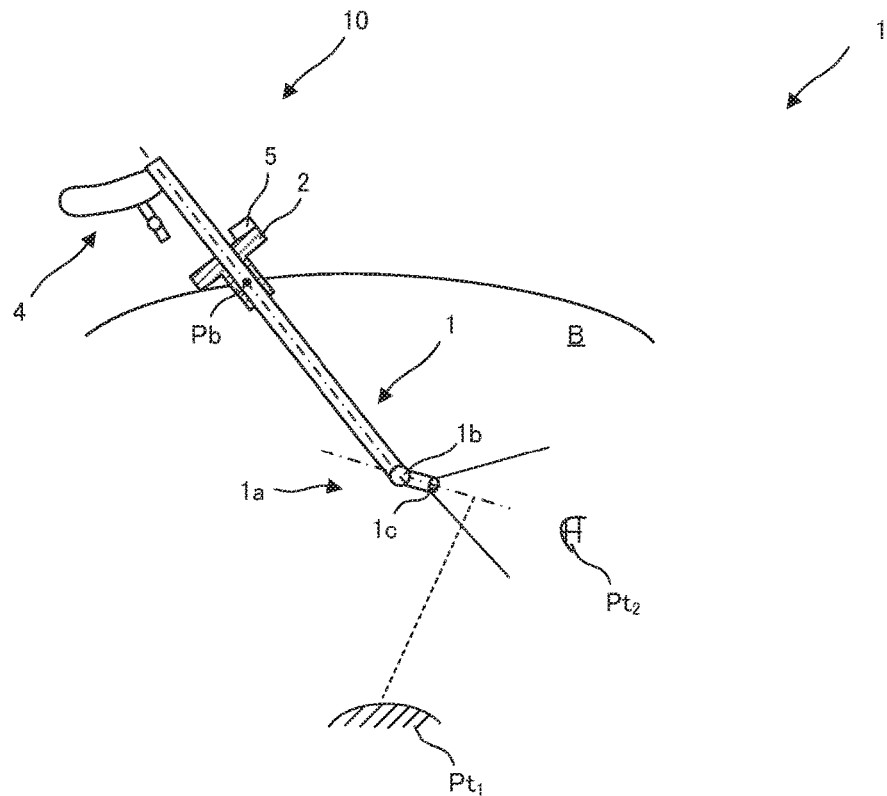
FIGS. 15A and 15B are illustrative of the endoscope in a state where there is the first subject of interest not present in the imaging range after movement of the endoscope system according to the second embodiment.
Figure 15B:
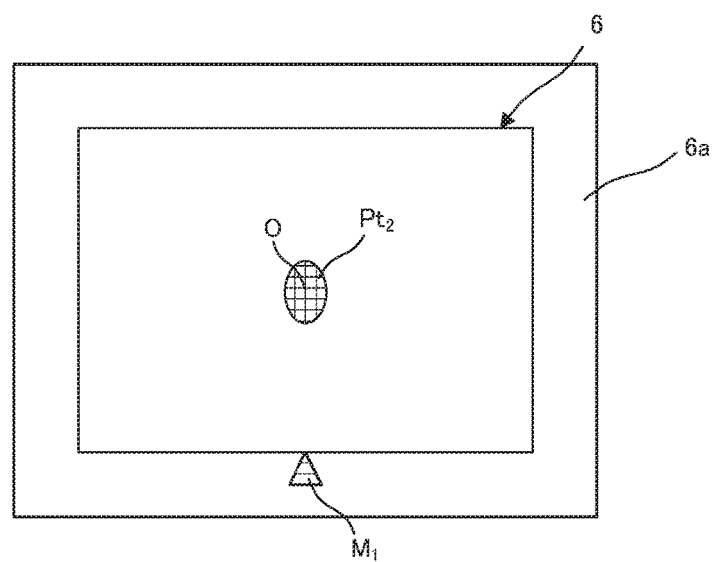

FIGS. 15A and 15B are illustrative of the endoscope 1 in the case where the first subject of interest $Pt_1$ is not within the imaging range after movement of the endoscope system 10 according to the second embodiment: FIG. 15A is illustrative of the endoscope system 10 and FIG. 15B is illustrative of the display unit 6.

Referring to FIGS. 15A and 15B, the endoscope 1 is taking an image of the second subject of interest $Pt_2$, but the first subject of interest $Pt_1$ does not then get into the imaging range.

The first direction indication mark $M_1$ appears on the edge 6a of the display unit 6 in the direction in which there is the first subject of interest $Pt_1$ present. The surgeon may look at the first direction indication mark $M_1$ for the purpose of easily keeping track of the direction in which there is the first subject of interest $Pt_1$ present, even when the first subject of interest $Pt_1$ is outside the imageable range.

In Step 17, when the tracking mode is held off by the switchover unit 77 and after going through Steps 16 and 19, the processing goes to Step 20 in which the counter is set to i=0 (ST20): the control gets done.

As described above, the endoscope system 10 according to the second method includes an endoscope 1 further including a field adjustment mechanism 1b for varying an orientation of the imaging unit 1a, an operation input unit 4 for operation of the field adjustment unit 1b and a driver unit 8 for driving the field adjustment mechanism, a driving-amount calculation unit 76 for computing an amount of driving the field adjustment mechanism 1b so as to display the subject of interest on the display unit 6, and a switchover unit 77 for switching between a follow-up mode of making the field adjustment mechanism 1b automatically drivable in association with a driving amount computed by the driving-amount calculation unit 76 and a manual mode of driving the field adjustment mechanism 1b based on an input from the operation input unit. It is thus easy to follow the subject of interest Pt automatically to take its image.

The present embodiment provides a process of controlling the endoscope 10 which process further includes an imaging range calculation step of computing an imaging range of the imaging unit 1a, wherein when the position of the subject of interest is outside the imaging range, the direction in which there is the subject of interest present in the display unit 6 is indicated in the direction indication step. It is possible for the surgeon to easily keep track of the direction in which there is the subject of interest present, even when the subject of interest gets out of the imageable range.

Figure 16:
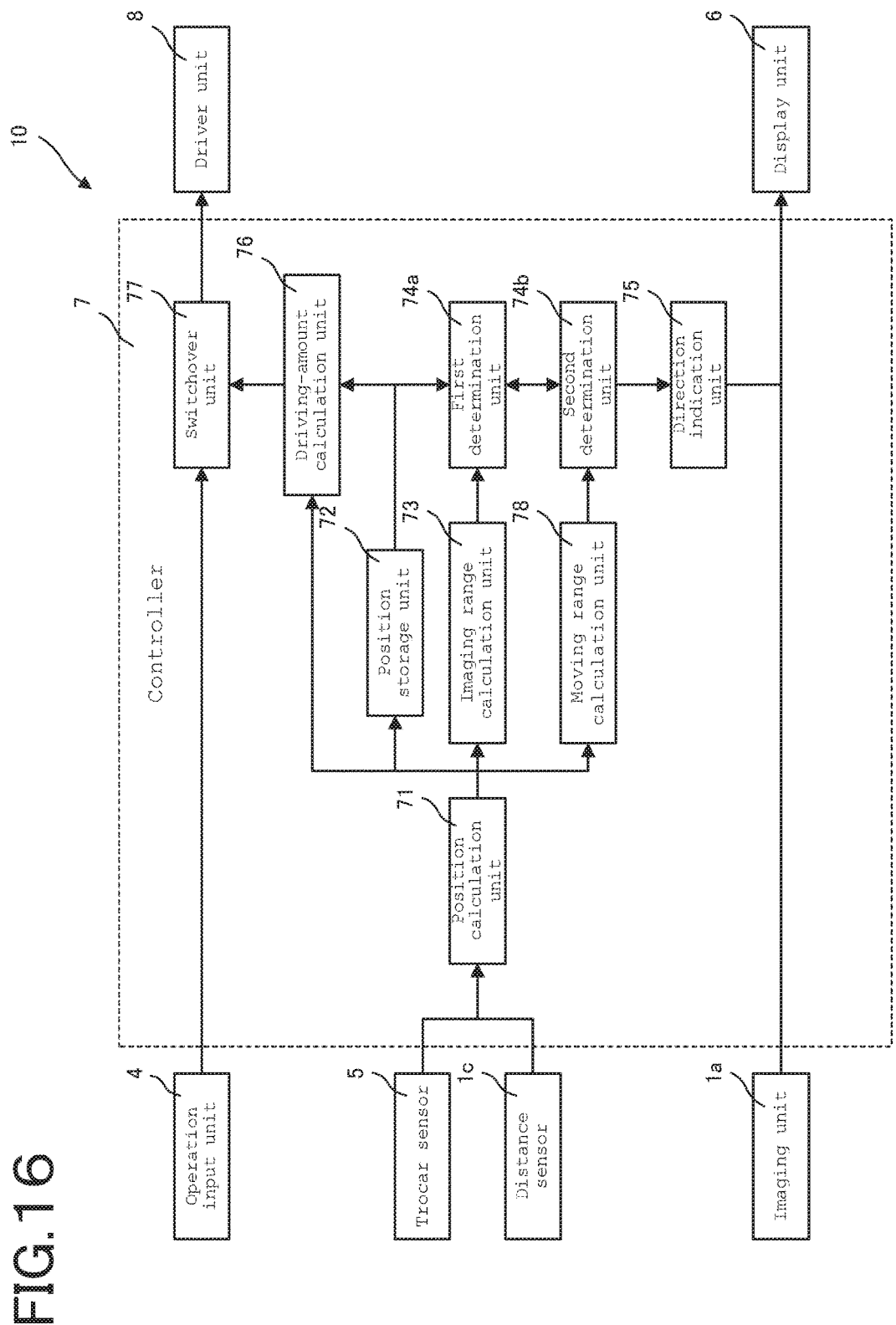
FIG. 16 is illustrative of one example of the control system for the endoscope system according to the third embodiment.

FIG. 16 is illustrative of one example of the control system for the endoscope system 10 according to the third embodiment.

The structure of the endoscope system 10 according to the third embodiment will not be explained anymore because of being similar to that of the endoscope system 10 according to the second embodiment. The position calculation 71, position storage unit 72, imaging range calculation unit 73, direction indication unit 75, driving-amount calculation unit 76 and switchover unit 77 in the endoscope system 10 according to the third embodiment will not again be explained because of being similar to those in the first embodiment.

The moving range of the field adjustment mechanism 1b of the endoscope 1 is computed by the moving-range calculation unit 78. It is thus possible to find the imageable range in which images may be taken upon driving of the field adjustment mechanism 1b of the endoscope 1. It is determined by the first determination unit 74a whether or not the position of the first subject of interest $Pt_1$ stored in the position storage unit 72 is included in the imaging range of the endoscope 1 found by the imaging range calculation unit 73 in which the endoscope 1 can take images in its current posture. It is determined by the second determination unit 74b whether or not the position of the first subject of interest $Pt_1$ stored in the position storage unit 72 is included in the imageable range of the endoscope 1 found by the moving range calculation unit 78.

Figure 17:
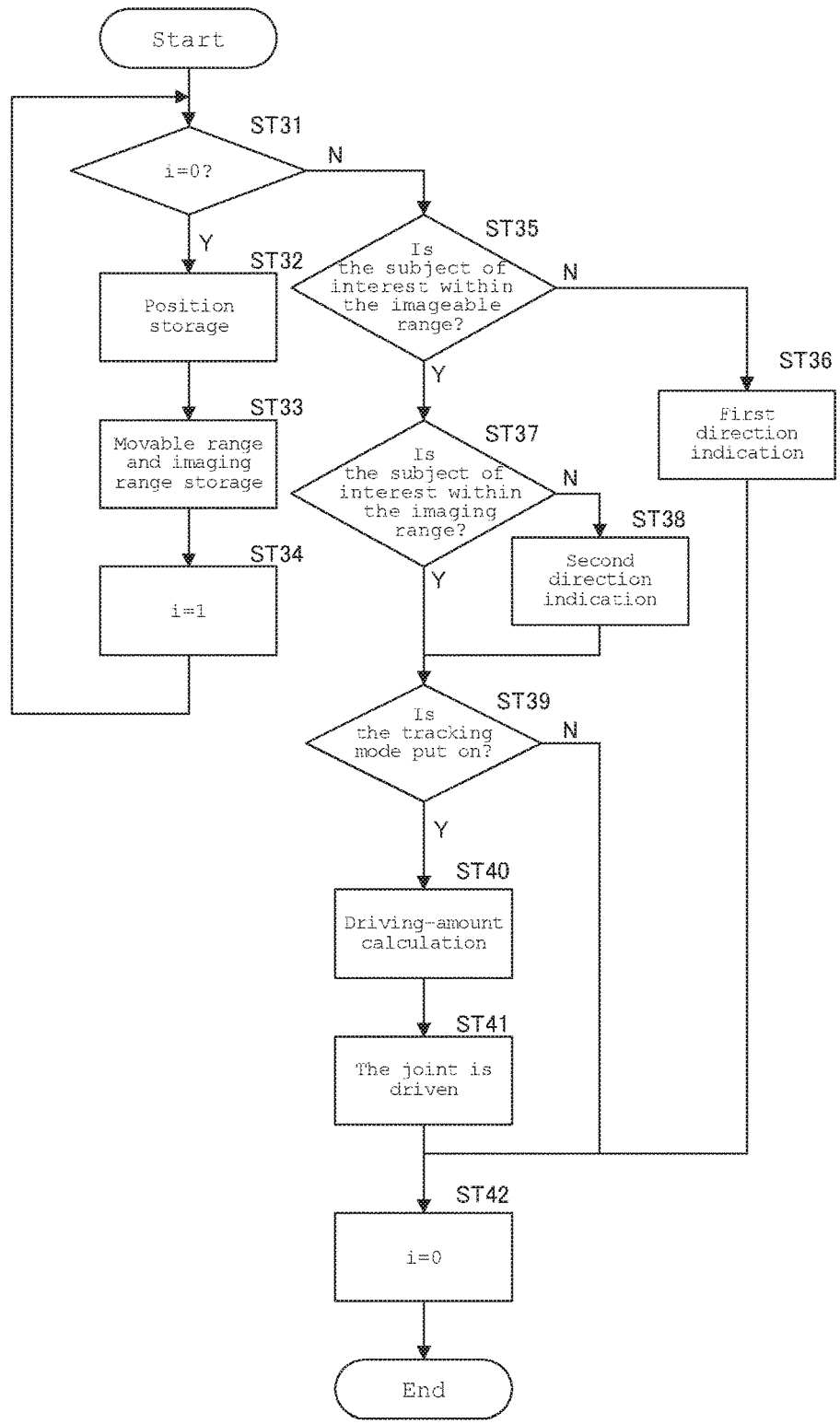
FIG. 17 is illustrative of one example of the control flowchart for the endoscope system according to the third embodiment.

FIG. 17 is illustrative of one example of the control flowchart for the endoscope system 10 according to the third embodiment.

Referring to the endoscope system 10 according to the third embodiment, it is first determined in Step 31 whether or not the counter is i=0 (ST31)

In Step 31, when the counter is i=0, the processing goes to Step 32 in which there is such a state as shown in FIG. 10 appearing: the positions of the distal end of the endoscope and the first subject of interest $Pt_1$ are computed by the position calculation unit 71 on the basis of information entered from the trocar sensor 5 and distance sensor 1c and then stored in the position storage unit 72 (ST32).

Then, the processing goes to Step 33 in which the imaging range is computed by the imaging range calculation unit 73 and the moving range is computed by the moving range calculation unit 78 (ST33). In other words, the imaging range in which the endoscope 1 can take images in its current posture is found together with the imageable range in which images can be taken upon the driving of the field adjustment mechanism 1b of the endoscope 1.

Then, the processing goes to Step 34 in which the counter is set to i=1 (ST34), and goes back to Step 31.

In Step 31, when the counter is not i=0, the processing goes to Step 35 in which it is determined whether or not the first subject of interest $Pt_1$ lies within the imageable range computed by the imaging range calculation unit 73 (ST35).

In Step 35, when the first subject of interest $Pt_1$ is not within the imageable range, the processing goes to Step 36 in which the direction indication mark $M_1$ is presented (ST36), and then goes to Step 42.

Figure 18A:
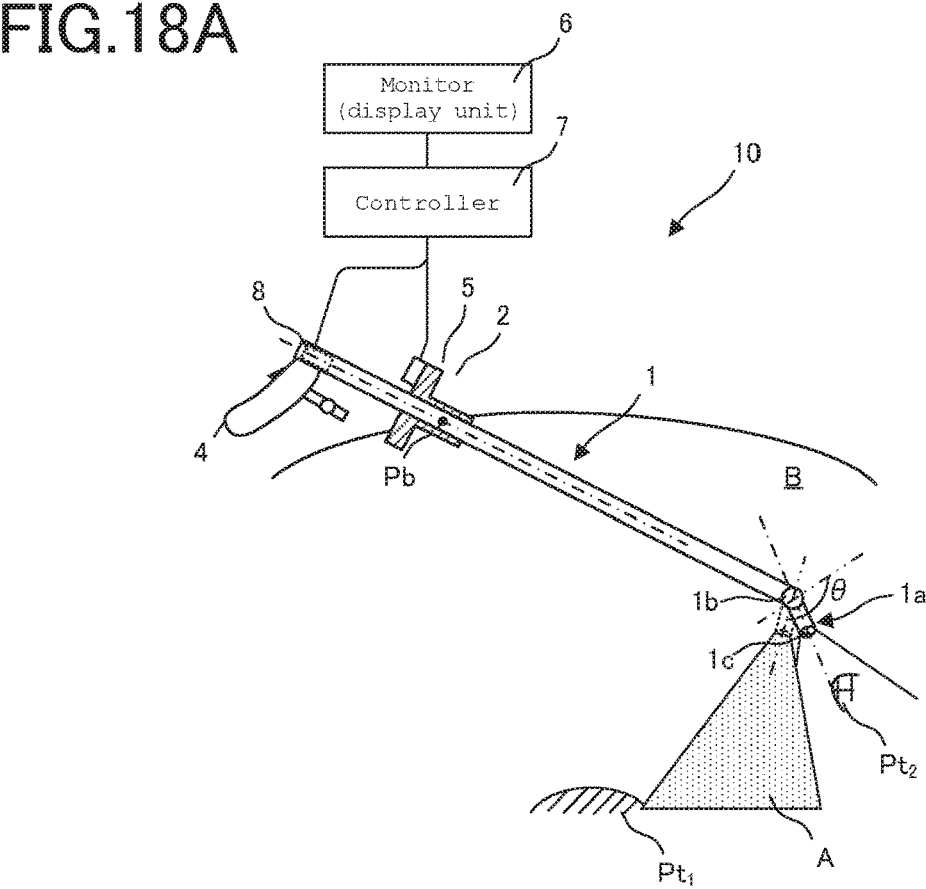
FIGS. 18A and 18B are illustrative of the endoscope in the endoscope system according to the third embodiment in a state where there is the first subject of interest getting out of the imageable range.
Figure 18B:
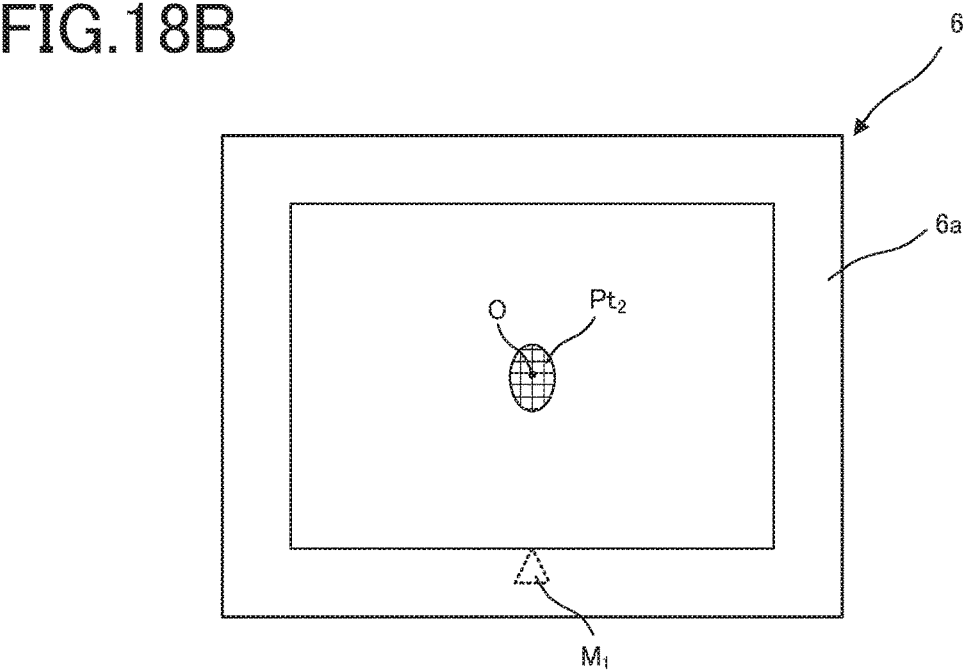

FIGS. 18A and 18B are illustrative of the endoscope 1 in which the first subject of interest $Pt_1$ is outside the imageable range in the endoscope system 10 according to the third embodiment: FIG. 18A is illustrative of the endoscope system 10 and FIG. 18B is illustrative of the display unit 6.

As shown in FIG. 18A, the first subject of interest $Pt_1$ is not included in an imaging range A, when the imaging unit 1a is rotated on the most first subject of interest $Pt_1$ side of a moving range θ of the field adjustment mechanism 1*b*. In this case, there is the first direction indication mark $M_1$ indicated on the outer circumference of the display unit 6 as an outside-the-imageable-range, as shown in FIG. 18B.

Such indication of the first direction indication mark $M_1$ on the outer circumference of the display unit 6 makes it possible for the surgeon to look at the first direction indication mark $M_1$ so as to keep track of which direction the first subject of interest $Pt_1$ lying outside the imageable range is in.

In Step 35, when the first subject of interest $Pt_1$ is within the imageable range, the processing goes to Step 37 in which it is determined whether or not the first subject of interest $Pt_1$ is within the imaging range (ST37).

In Step 37, when the first subject of interest $Pt_1$ is not within the imaging range, the processing goes to Step 38 in which the second direction indication mark $M_2$ is presented (ST38), and then goes to Step 39.

Figure 19A:
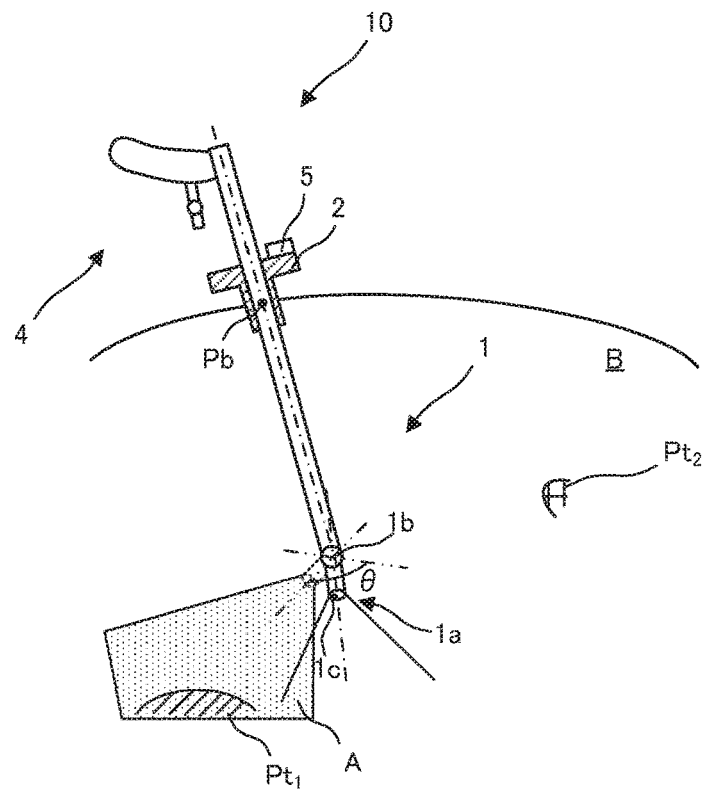
FIGS. 19A and 19B are illustrative of the endoscope in the endoscope system according to the third embodiment in a state where there is the first subject of interest present within the imageable range and getting out of the imaging range.
Figure 19B:
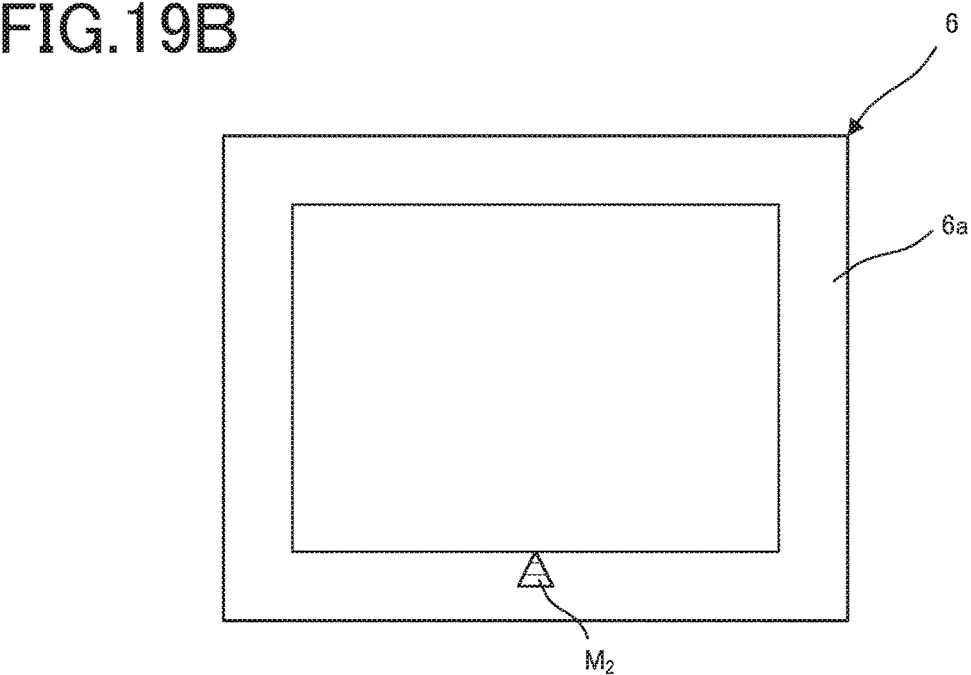

FIGS. 19A and 19B are illustrative of the endoscope 1 in the case where the first subject of interest $Pt_1$ is within the imageable range and outside the imaging range in the endoscope system 10 according to the third embodiment: FIG. 19A is illustrative of the endoscope system 10 and FIG. 19B is illustrative of the display unit 6.

As shown in FIG. 19A, the first subject of interest $Pt_1$ is outside the imageable range, but the first subject of interest $Pt_1$ is included in the imaging range A, when the imaging unit 1*a* is rotated on the most first subject of interest $Pt_1$ side of the moving range θ of the field adjustment mechanism 1*b*. In this case, there is the second direction indication mark $M_2$ indicated on the edge 6*a* of the display unit 6 as an inside-the-imageable-range, as shown in FIG. 19B.

Such indication of the second direction indication mark $M_2$ on the edge 6*a* of the display unit 6 makes it possible for the surgeon to look at the second direction indication mark $M_2$ so as to keep track of which direction the first subject of interest $Pt_1$ lying within the imageable range is in, although the first subject of interest $Pt_1$ is outside the imaging range.

In Step 37, when the first subject of interest Pt1 is within the imaging range or in Step 38, when the second direction indication mark M2 is presented, the processing goes to Step 39 in which it is determined whether or not the tracking mode is held on by the switchover unit 77 (ST39).

In step 39, when the tracking mode is held on by the switchover unit 77, the processing goes to Step 40 in which the driving amount computed by the driving-amount calculation unit 76 is computed (ST40), and then goes to Step 41 in which the joint is driven according to the computed driving amount (ST41).

It is thus possible for the surgeon to put on the tracking mode even when the first subject of interest $Pt_1$ gets out of the field of view. In turn, this enables the field adjustment mechanism 1*b* to be driven without recourse to any operation and, hence, the imaging unit 1*a* to take an image of the subject of interest $Pt_1$, resulting in improvements in operability.

In Step 39, when the tracking mode is held off by the switchover unit 77 and after going through Step 36 and Step 41, the processing goes to Step 42 in which the counter is set to i=0 (ST42): the control gets done.

In the endoscope system 10 according to the third embodiment, the first direction indication mark $M_1$ indicating that the first subject of interest $Pt_1$ gets out of the imageable range and the second direction indication mark $M_2$ may be used to indicate that the first subject of interest $Pt_1$ is outside the imaging range but within the imageable range. Referring to a specific case where the first subject of interest $Pt_1$ is outside the imaging range but within the imageable range, the direction indication marks may be provided depending on whether or not the subject of interest $Pt_1$ may be moved to a position including the center of the display unit 6.

As described above, the endoscope system 10 according to the third embodiment includes an endoscope 1 further including a field adjustment mechanism 1*b* for varying an orientation of the imaging unit 1*a*, an operation input unit 4 for operation of the field adjustment unit 1*b* and a driver unit 8 for driving the field adjustment mechanism 1*b*, and further includes an imaging range calculation unit 73 for computing an imaging range of the imaging unit 1*a*, a first determination unit 74*a* for determining whether or not the position of the subject of interest is within the imaging range, a moving range calculation unit 78 for computing a moving range of the field adjustment mechanism 1*b*, a second determination unit 74*b* for determining whether or not the position of the subject of interest is within an imageable range, a driving-amount calculation unit 76 for computing an amount of driving the field adjustment mechanism 1*b* so as to display the subject of interest on the display unit 6, and a switchover unit 77 for switching between a follow-up mode of making the field adjustment mechanism 1*b* automatically drivable in association with a driving amount computed by the driving-amount calculation unit 76 and a manual mode of driving the field adjustment mechanism 1*b* based on an input from the operation input unit, and wherein when the position of the subject of interest is determined by the first determination unit 74*a* as being outside the imaging range and the position of the subject of interest is determined by the second determination unit 74*b* as being outside the imageable range, the direction indication unit 75 displays a first direction indication mark $M_1$ indicative of a direction of the position on the display unit 6, and when the position of the subject of interest is determined by the first determination unit 74*a* as being outside the imaging range and the position of the subject of interest is determined by the second determination unit 74*b* as being within the imageable range, the direction indication unit 75 displays a second direction indication mark $M_2$ indicative of a direction of the position on the display unit 6. It is thus possible to indicate the direction of the subject of interest thereby easily keeping and unerring track of the position of the subject of interest.

According to the embodiment, when the position of the subject of interest is determined by the first determination unit 74*a* as being outside the imaging range and the position of the subject of interest is determined by the second determination unit 74*b* as being within the imageable range, the switchover unit 77 switches the driving unit 8 over to the follow-up mode, and when the position of the subject of interest is determined by the first determination unit 74*a* as being outside the moving range and the position of the subject of interest is determined by the second determination unit 74*b* as being outside the imaging range, the switchover unit 77 switches the driving unit 8 over to the manual mode. When there is the subject of interest present in a range to be not followed, it is thus possible to indicate the direction of the subject of interest thereby keeping easy and unerring track of the position of the subject of interest, and when there is the subject of interest present in a range to be followed, it is thus possible to keep automatic track of the subject of interest and easily take its image.

The process of controlling the endoscope system 10 including an endoscope 1 further including a field adjustment mechanism 1*b* for varying the orientation of an imaging unit 1*a* further includes a driving-amount calculation step for computing the amount of driving the field adjustment mechanism 1b so as to display the subject of interest on the display unit 6 and a follow-up step of driving the field adjustment mechanism 1b according to the driving amount to allow the endoscope 1 to follow the subject of interest. It is thus possible to keep automatic track of the subject of interest and easily take its image.

Figure 20A:
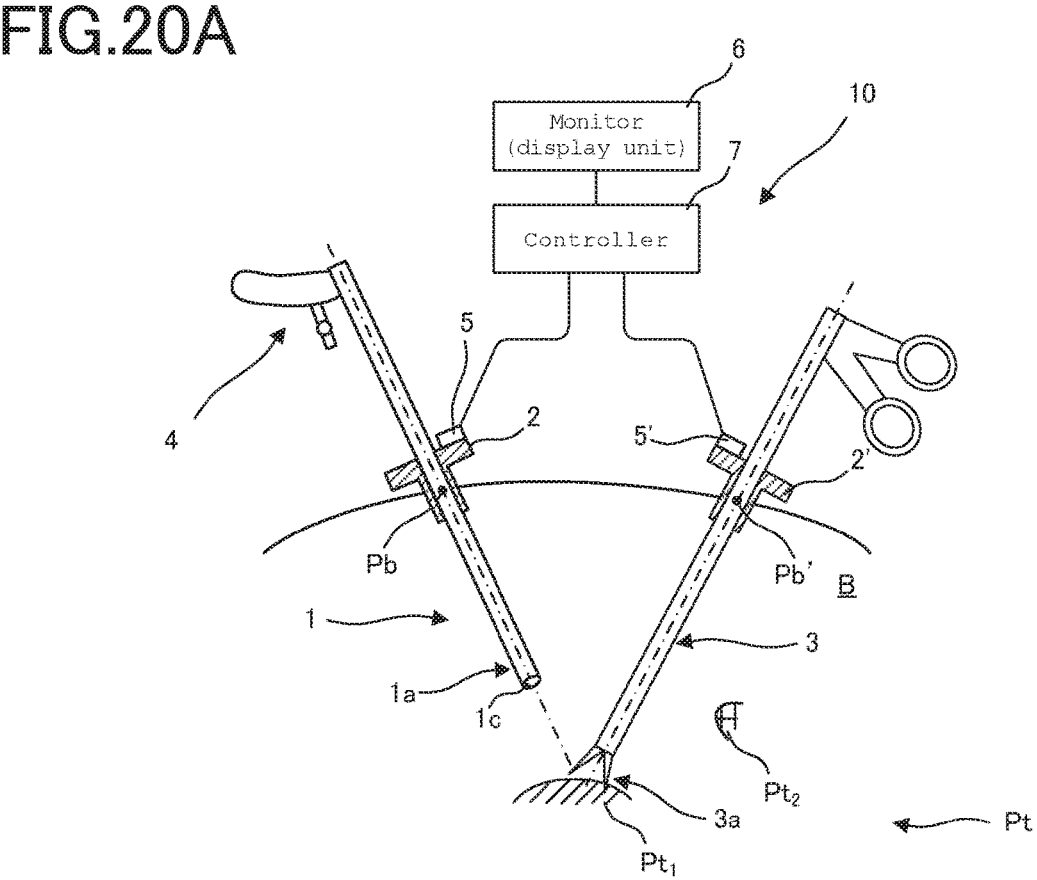
FIGS. 20A and 20B are a schematic view of one example of the endoscope system according to the fourth embodiment.
Figure 20B:
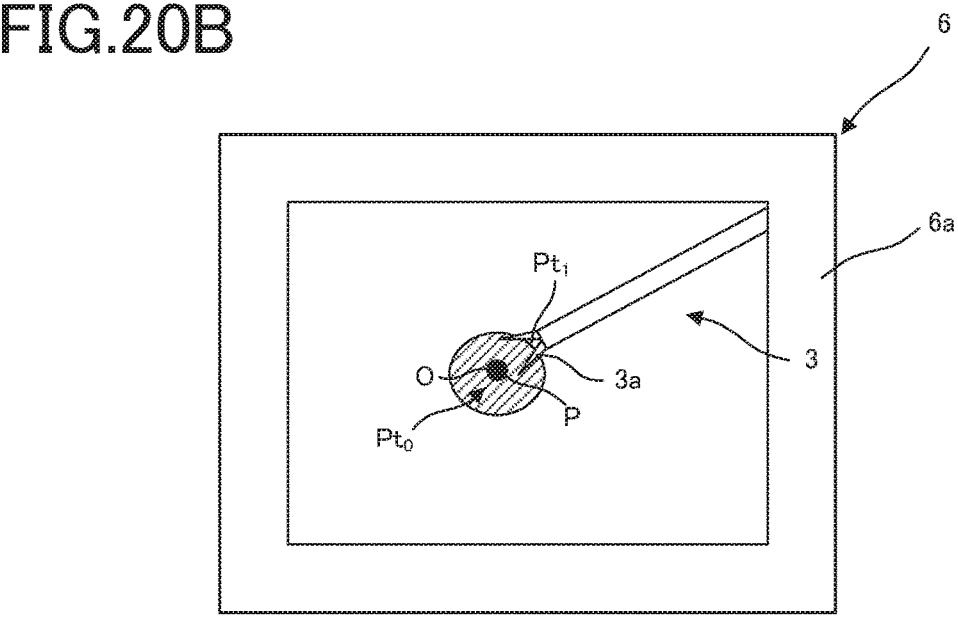

FIGS. 20A and 20B are a schematic view of one example of the endoscope system 10 according to the fourth embodiment: FIG. 20A is illustrative of the endoscope system 10 and FIG. 20B is illustrative of the display unit 6.

Figure 21A:
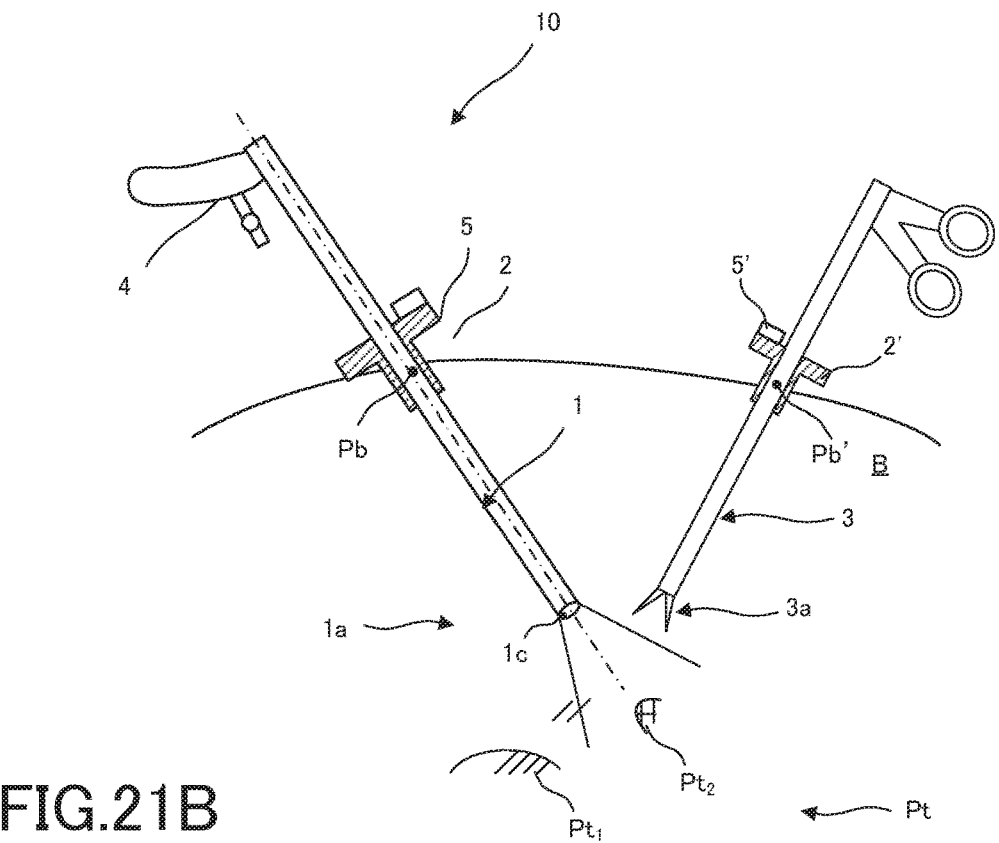
FIGS. 21A and 21B are illustrative of the endoscope system according to the fourth embodiment wherein the endoscope is directed to the second subject of interest.
Figure 21B:
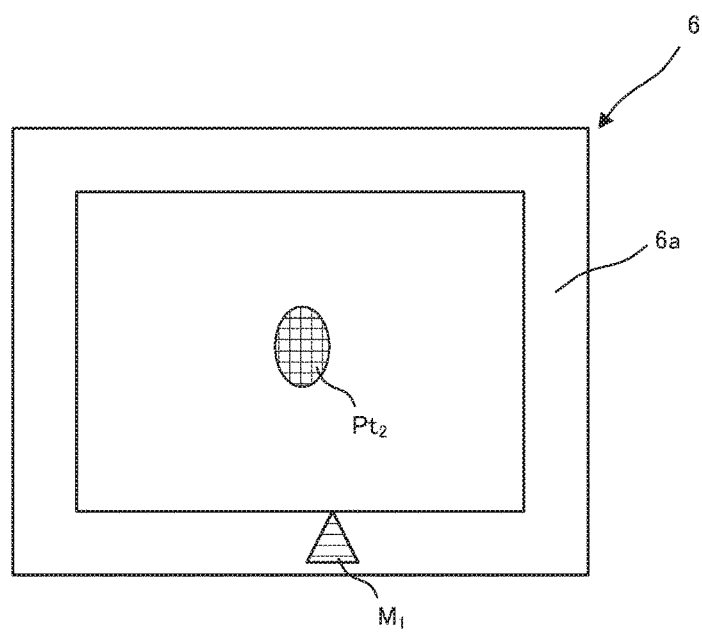

FIGS. 21A and 21B are illustrative of a state in which the endoscope 1 according to the fourth embodiment is directed to the second subject of interest $Pt_e$: FIG. 21A is illustrative of the endoscope system 10 and FIG. 21B is illustrative of the display unit 6.

In the endoscope system 10 according to the fourth embodiment, a location where there is the distal end 3a of a treatment tool 3 is stored.

As shown in FIG. 20A, a second trocar 2' through which the treatment tool 3 is inserted is rotatable about a fulcrum Pb', and a second trocar sensor 5' working as a second position sensor is capable of detecting at least the tilt angle of the second trocar 2' and the amount of insertion of the treatment tool 3 through the second trocar 2'.

The endoscope 1 is inserted into the body cavity B through the trocar 2, and the imaging unit 1a of the endoscope 1 is directed to the first subject of interest $Pt_1$ by operation of the operation input unit 4.

The trocar 2 is also rotatable about the fulcrum Pb, and the trocar sensor 5 working as a position sensor is capable of detecting at least the tilt angle of the trocar 2, the amount of insertion of the endoscope 1 through the trocar 2 and the angle of rotation of the endoscope 1 with respect to the center axis, as is the case with the first embodiment.

While the trocar sensor 5 is used as the position sensor in the fourth embodiment, it is to be understood that other sensor may also be used provided that it is capable of detecting the position of the endoscope 1 within the body cavity B. It is also to be noted that the control system for the endoscope system 10 according to the fourth embodiment may be similar to that for the first embodiment shown in FIG. 4.

Referring to the endoscope system 10 according to the fourth embodiment, the positions of the distal end of the endoscope, the distal end of the treatment tool and the first subject of interest $Pt_1$ are computed by the position calculation unit 71 in such a state as shown in FIGS. 20A and 20B, on the basis of information entered from the trocar sensor 5 and the second trocar sensor 5', and those positions are stored in the position storage unit 72.

After that, shown in FIGS. 21A and 21B, it assumes here that an image of the second subject of interest $Pt_2$ is taken by the surgeon. In the endoscope system 10 according to the fourth embodiment, it is determined whether or not the first subject of interest $Pt_1$ is within the imaging range computed by the imaging range calculation unit 73. When the first subject of interest $Pt_1$ is not within the imaging range, there is the first direction indication mark $M_1$ displayed.

As described above, the endoscope system 10 according to the fourth embodiment includes a treatment tool 3 for applying treatments to the body cavity, and a treatment tool position sensor (second trocar sensor) 5' for measuring a position of a distal end of the treatment tool, wherein the position calculation unit 71 computes the position of the subject of interest on the basis of information from the treatment tool position sensor 5', and the position storage unit 72 stores the position of the subject of interest computed by the position calculation unit 71. It is thus possible to determine a site coming into direct contact with the treatment tool 3 as a pertinent position for more institutive operation.

Figure 22:
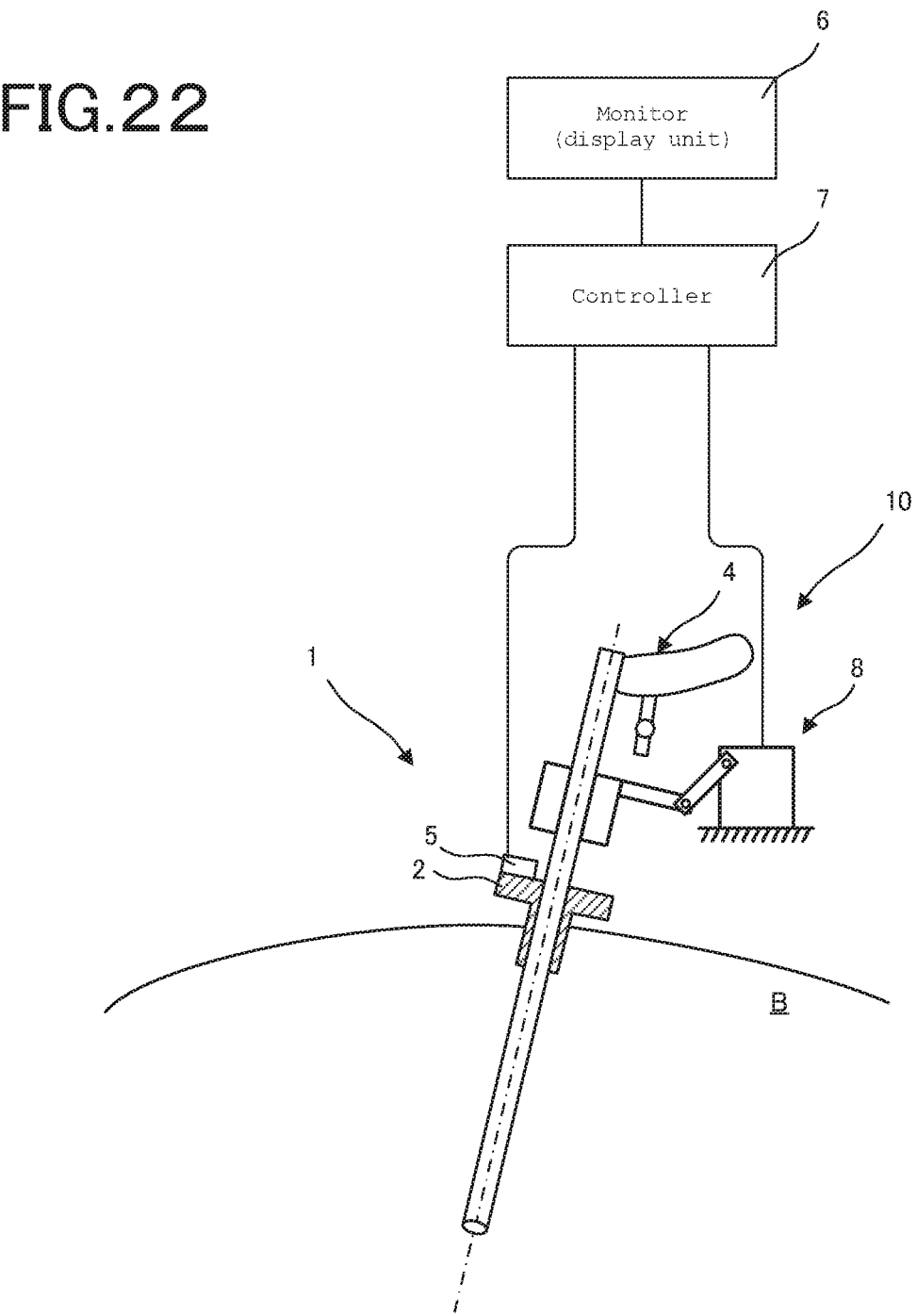
FIG. 22 is a schematic view of the endoscope system 10 according to a further embodiment.

FIG. 22 is a schematic view of one example of the endoscope system 10 according to a further embodiment.

In the example shown in FIG. 22, the driver unit 8 for the endoscope 1 is located outside the body cavity. In the driver unit 8, an actuator may be used to drive the endoscope 1 in a advanceable/retractable movement direction, a tilting direction, and a rotational direction with respect to an axial center.

The endoscope system 10 according to the embodiments described herein may also be embodied in other possible forms.

For instance, multiple positions may be stored in the position storage unit 72 with a selection unit for selecting the position to be followed out of the stored multiple positions. In this case, names may be given to the stored multiple positions to display them on the display unit 6. Alternatively, in the vicinity of the direction indication mark, the name of a position corresponding to that direction indication mark may be displayed. While the hard endoscope 1 has been taken as an example in the present disclosure, it is to be understood that a flexible or soft endoscope may also be used.

In the endoscope system 10 according to the embodiment described herein, it is possible to take an unerring image of the subject of interest, because in the follow-up mode, the field adjustment mechanism 1b is driven by the driver unit 8 such that the subject of interest is displayed in a position including the center of the display unit 6.

According to the embodiment described herein, the position storage unit 72 is capable of storing positions of a plurality of the subjects of interest, and includes a selection unit for selecting which of the plurality of the subjects of interest is to be followed. It is thus possible to take the selected subject of interest unerringly.

According to the embodiment described herein, when the position of the subject of interest is outside the imaging range, the direction indication mark is displayed by the direction indication unit 75 on the edge 6a of the display unit 6. Thus, the direction indication mark is unlikely to block the screen on which there are images appearing.

According to the embodiment described herein, when the position of the subject of interest is within the imaging range, the direction indication unit 75 produces a point mark P display while superimposed on the subject of interest displayed by the display unit 6. It is thus possible to keep easy track of the subject of interest.

In the embodiments described herein, while parameters such as position coordinates and driving amounts are figured out by giving input values to a variety of preset mathematical formulae, it is to be appreciated that the desired numerical values may be derived with reference to a preset lookup table (correspondence table) with the input values as key or, alternatively, mathematical formulae may be combined with the table.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Endoscope
1a: Imaging unit
1b: Field adjustment mechanism
1c: Distance sensor
2: Trocar
3: Treatment tool
4: Operation input unit
5: Trocar sensor (endoscopic position sensor)
7: Control unit
71: Position calculation unit
72: Position storage unit
73: Imaging range calculation unit
74: Determination unit
74a: First determination unit
74b: Second determination unit
75: Direction indication unit
76: Driving-amount calculation unit
77: Switchover unit
78: Moving range calculation unit
8: Driver unit
10: Endoscope system

The invention claimed is:

1. An endoscope system comprising:
an endoscope comprising an image sensor arranged at a distal end of the endoscope, wherein the image sensor is configured to capture an image of a subject of interest in a body cavity within an imaging range of the image sensor;
an endoscopic position sensor configured to perform detections of positions of the endoscope in the body cavity;
a distance sensor configured to perform detections of distances from the distal end of the endoscope to the subject of interest;
a field adjusting actuator configured to vary an orientation of the image sensor within a moving range of the field adjusting actuator to move the imaging range of the image sensor within an imageable range;
a driver configured to drive the field adjusting actuator to vary the orientation of the image sensor within the moving range of the field adjusting actuator to move the imaging range of the image sensor within the imageable range; and
a processor comprising hardware, wherein the processor is configured to:
 receive an initial position of the endoscope in the body cavity detected by the endoscopic position sensor and an initial distance from the distal end of the endoscope to the subject of interest detected by the distance sensor;
 determine, based on the initial position of the endoscope in the body cavity, the initial distance from the distal end of the endoscope to the subject of interest, and the moving range of the field adjusting actuator, whether a current position of the subject of interest is within the imageable range;
 in response to determining that the current position of the subject of interest is not within the imageable range:
  calculate a first direction in which the current position of the subject of interest is positioned relative to a current imaging range of the image sensor; and
  control a display to display a first direction indication indicative of the first direction;
 in response to determining that the current position of the subject of interest is within the imageable range:
  determine whether the current position of the subject of interest is within the current imaging range of the image sensor; and
  in response to determining that the current position of the subject of interest is not within the current imaging range of the image sensor:
   calculate a second direction in which the current position of the subject of interest is positioned relative to the current imaging range of the image sensor; and
   control the display to display a second direction indication indicative of the second direction,
wherein the processor is configured to:
 in response to determining that the current position of the subject of interest is not within the imageable range:
  receive a user input; and
  control the driver to drive the field adjusting actuator to vary the orientation of the image sensor based on the user input; and
 in response to determining that the current position of the subject of interest is within the imageable range and determining that the current position of the subject of interest is within the current imaging range of the image sensor:
  calculate a driving amount by which the driver is to drive the field adjusting actuator to vary the orientation of the image sensor within the moving range of the field adjusting actuator to move the imaging range of the image sensor so that the subject of interest is within the imaging range of the image sensor; and
  control the driver to drive the field adjusting actuator based on the driving amount calculated.

2. The endoscope system according to claim 1, wherein the processor is configured to:
in response to determining that the current position of the subject of interest is within the imageable range and determining that the current position of the subject of interest is within the current range of the image sensor:
 calculate the driving amount by which the driver is to drive the field adjusting actuator to vary the orientation of the image sensor within the moving range of the field adjusting actuator to move the imaging range of the image sensor so that the subject of interest is positioned at a center of the display.

3. The endoscope system according to claim 1, wherein the processor is configured to:
control a storage to store positions of a plurality of possible subjects of interest; and
select which of the plurality of possible subjects of interest is to be the subject of interest.

4. The endoscope system according to claim 1, wherein the processor is configured to control the display to display the first direction indication and the second direction indication at an edge of the display.

5. The endoscope system according to claim 1,
wherein the processor is configured to, in response to determining that the current position of the subject of interest is within the current imaging range of the image sensor, control the display to display a point mark while superimposed on the subject of interest displayed on the display.

6. The endoscope system according to claim 1, comprising:
a treatment tool configured to apply a treatment within the body cavity; and
a treatment tool position sensor configured to perform detections of positions of a distal end of the treatment tool,
wherein the processor is configured to calculate positions of the subject of interest based on the positions of the distal end of the treatment tool detected by the treatment tool position sensor.

7. A method of controlling an endoscope system comprising:
an endoscope comprising an image sensor arranged at a distal end of the endoscope, wherein the image sensor is configured to capture an image of a subject of interest in a body cavity within an imaging range of the image sensor;
an endoscopic position sensor configured to perform detections of positions of the endoscope in the body cavity;
a distance sensor configured to perform detections of distances from the distal end of the endoscope to the subject of interest;
a field adjusting actuator configured to vary an orientation of the image sensor within a moving range of the field adjusting actuator to move the imaging range of the image sensor within an imageable range; and
a driver configured to drive the field adjusting actuator to vary the orientation of the image sensor within the moving range of the field adjusting actuator to move the imaging range of the image sensor within the imageable range,
wherein the method comprises:
receiving an initial position of the endoscope in the body cavity detected by the endoscopic position sensor and an initial distance from the distal end of the endoscope to the subject of interest detected by the distance sensor;
determining, based on the initial position of the endoscope in the body cavity, the initial distance from the distal end of the endoscope to the subject of interest, and the moving range of the field adjusting actuator, whether a current position of the subject of interest is within the imageable range;
in response to determining that the current position of the subject of interest is not within the imageable range:
calculating a first direction in which the current position of the subject of interest is positioned relative to a current imaging range of the image sensor; and
controlling a display to display a first direction indication indicative of the first direction;
in response to determining that the current position of the subject of interest is within the imageable range:
determining whether the current position of the subject of interest is within the current imaging range of the image sensor; and
in response to determining that the current position of the subject of interest is not within the current imaging range of the image sensor:
calculating a second direction in which the current position of the subject of interest is positioned relative to the current imaging range of the image sensor; and
controlling the display to display a second direction indication indicative of the second direction,
wherein the method comprises:
in response to determining that the current position of the subject of interest is not within the imageable range:
receiving a user input; and
controlling the driver to drive the field adjusting actuator to vary the orientation of the image sensor based on the user input; and
in response to determining that the current position of the subject of interest is within the imageable range and determining that the current position of the subject of interest is within the current imaging range of the image sensor:
calculating a driving amount by which the driver is to drive the field adjusting actuator to vary the orientation of the image sensor within the moving range of the field adjusting actuator to move the imaging range of the image sensor so that the subject of interest is within the imaging range of the image sensor; and
controlling the driver to drive the field adjusting actuator based on the driving amount calculated.

8. A non-transitory computer-readable storage medium storing instructions for controlling an endoscope system comprising:
an endoscope comprising an image sensor arranged at a distal end of the endoscope, wherein the image sensor is configured to capture an image of a subject of interest in a body cavity within an imaging range of the image sensor;
an endoscopic position sensor configured to perform detections of positions of the endoscope in the body cavity;
a distance sensor configured to perform detections of distances from the distal end of the endoscope to the subject of interest;
a field adjusting actuator configured to vary an orientation of the image sensor within a moving range of the field adjusting actuator to move the imaging range of the image sensor within an imageable range; and
a driver configured to drive the field adjusting actuator to vary the orientation of the image sensor within the moving range of the field adjusting actuator to move the imaging range of the image sensor within the imageable range,
wherein the instructions cause a computer to at least perform:
receiving an initial position of the endoscope in the body cavity detected by the endoscopic position sensor and an initial distance from the distal end of the endoscope to the subject of interest detected by the distance sensor;
determining, based on the initial position of the endoscope in the body cavity, the initial distance from the distal end of the endoscope to the subject of interest, and the moving range of the field adjusting actuator, whether a current position of the subject of interest is within the imageable range;
in response to determining that the current position of the subject of interest is not within the imageable range:
calculating a first direction in which the current position of the subject of interest is positioned relative to a current imaging range of the image sensor; and
controlling a display to display a first direction indication indicative of the first direction;
in response to determining that the current position of the subject of interest is within the imageable range:
determining whether the current position of the subject of interest is within the current imaging range of the image sensor; and
in response to determining that the current position of the subject of interest is not within the current imaging range of the image sensor:
calculating a second direction in which the current position of the subject of interest is positioned relative to the current imaging range of the image sensor; and
controlling the display to display a second direction indication indicative of the second direction,
wherein the instructions cause the computer to perform:
in response to determining that the current position of the subject of interest is not within the imageable range:
receiving a user input; and
controlling the driver to drive the field adjusting actuator to vary the orientation of the image sensor based on the user input; and
in response to determining that the current position of the subject of interest is within the imageable range and determining that the current position of the subject of interest is within the current imaging range of the image sensor:
calculating a driving amount by which the driver is to drive the field adjusting actuator to vary the orientation of the image sensor within the moving range of the field adjusting actuator to move the imaging range of the image sensor so that the subject of interest is within the imaging range of the image sensor; and
controlling the driver to drive the field adjusting actuator based on the driving amount calculated.

9. An endoscope system comprising:
an endoscope comprising an image sensor arranged at a distal end of the endoscope, wherein the image sensor is configured to capture an image of a subject of interest in a body cavity within an imaging range of the image sensor;
an endoscopic position sensor configured to perform detections of positions of the endoscope in the body cavity;
a distance sensor configured to perform detections of distances from the distal end of the endoscope to the subject of interest;
a field adjusting actuator configured to vary an orientation of the image sensor within a moving range of the field adjusting actuator to move the imaging range of the image sensor within an imageable range;
a driver configured to drive the field adjusting actuator to vary the orientation of the image sensor within the moving range of the field adjusting actuator to move the imaging range of the image sensor within the imageable range; and
a processor comprising hardware, wherein the processor is configured to:
receive an initial position of the endoscope in the body cavity detected by the endoscopic position sensor and an initial distance from the distal end of the endoscope to the subject of interest detected by the distance sensor;
determine, based on the initial position of the endoscope in the body cavity, the initial distance from the distal end of the endoscope to the subject of interest, and the moving range of the field adjusting actuator, whether a current position of the subject of interest is within the imageable range;
in response to determining that the current position of the subject of interest is not within the imageable range:
calculate a first direction in which the current position of the subject of interest is positioned relative to a current imaging range of the image sensor; and
control a display to display a first direction indication indicative of the first direction;
in response to determining that the current position of the subject of interest is within the imageable range:
determine whether the current position of the subject of interest is within the current imaging range of the image sensor; and
in response to determining that the current position of the subject of interest is not within the current imaging range of the image sensor:
calculate a second direction in which the current position of the subject of interest is positioned relative to the current imaging range of the image sensor; and
control the display to display a second direction indication indicative of the second direction,
wherein the processor is configured to:
in response to determining that the current position of the subject of interest is within the imageable range and determining that the current position of the subject of interest is within the current imaging range of the image sensor:
calculate a driving amount by which the driver is to drive the field adjusting actuator to vary the orientation of the image sensor within the moving range of the field adjusting actuator to move the imaging range of the image sensor so that the subject of interest is within the imaging range of the image sensor; and
control the driver to drive the field adjusting actuator based on the driving amount calculated.

* * * * *